US010709624B2

(12) United States Patent
Bhimavarapu et al.

(10) Patent No.: US 10,709,624 B2
(45) Date of Patent: Jul. 14, 2020

(54) COMMUNICATION METHODS FOR PATIENT HANDLING DEVICES

(71) Applicant: Stryker Corporation, Kalamazoo, MI (US)

(72) Inventors: Krishna Sandeep Bhimavarapu, Portage, MI (US); Christopher J. Cummings, Portage, MI (US); Jonathan Mark Greenbank, Plainwell, MI (US); Michael Joseph Hayes, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 445 days.

(21) Appl. No.: 14/622,221

(22) Filed: Feb. 13, 2015

(65) Prior Publication Data

US 2015/0231006 A1    Aug. 20, 2015

Related U.S. Application Data

(60) Provisional application No. 61/940,092, filed on Feb. 14, 2014.

(51) Int. Cl.
*A61G 7/018*     (2006.01)
*G16H 40/63*    (2018.01)
(Continued)

(52) U.S. Cl.
CPC .............. *A61G 7/018* (2013.01); *G16H 40/63* (2018.01); *G06F 19/3418* (2013.01); *G16H 40/20* (2018.01)

(58) Field of Classification Search
CPC ............... G06F 19/3418; G06F 19/327; G06F 19/3406; A61G 7/018; G16H 40/20; G16H 40/63
See application file for complete search history.

(56) References Cited

U.S. PATENT DOCUMENTS 5,715,548 A * 2/1998 Weismiller ........... A61G 7/0527
                                                          5/611
5,771,511 A * 6/1998 Kummer ................ A61G 7/015
                                                          5/424
(Continued)

FOREIGN PATENT DOCUMENTS

WO    2012122002 A1    9/2012
WO    2014150970 A1    9/2014

OTHER PUBLICATIONS

International Search Report for PCT/US2015/015889, the international counterpart to U.S. Appl. No. 14/622,221.
(Continued)

*Primary Examiner* — Nicholas F Polito
*Assistant Examiner* — Amanda L Bailey
(74) *Attorney, Agent, or Firm* — Warner Norcross + Judd LLP

(57) ABSTRACT

Patient care devices, such as person support apparatuses and thermal control units, include one or more internal high speed networks, such as an Ethernet, for transmitting data between internal nodes or modules. A lower speed network may also be included with the Ethernet for redundantly transmitting some, but not all, types of data. Devices external to the patient care device can be granted limited access to the internal high speed network. Such devices may connect to the high speed network to utilize one or more user interfaces of the patient care device and/or to piggyback onto the patient care device's connection to an external local area network (e.g. a hospital LAN), or the patient care device's connection to yet another device. Some nodes may include web servers for serving up web pages of diagnostic information relevant to that node. The web servers are accessible via an external web browser.

19 Claims, 11 Drawing Sheets

(51) Int. Cl.
*G16H 40/20* (2018.01)
*G06F 19/00* (2018.01)

(56) References Cited

U.S. PATENT DOCUMENTS

| | | | |
|---|---|---|---|
| 7,296,312 B2* | 11/2007 | Menkedick | A61B 5/1115 |
| | | | 5/600 |
| 8,314,781 B2* | 11/2012 | Pittenger | G05B 19/414 |
| | | | 178/18.06 |
| 8,674,826 B2 | 3/2014 | Becker et al. | |
| 9,320,662 B2 | 4/2016 | Hayes et al. | |
| 2009/0188731 A1* | 7/2009 | Zerhusen | A61G 7/05 |
| | | | 180/19.3 |
| 2011/0205061 A1 | 8/2011 | Wilson et al. | |
| 2011/0210925 A1 | 9/2011 | Pittenger et al. | |
| 2011/0224510 A1* | 9/2011 | Oakhill | A61B 5/11 |
| | | | 600/301 |
| 2012/0235830 A1 | 9/2012 | Becker et al. | |
| 2013/0283529 A1 | 10/2013 | Hayes et al. | |
| 2013/0318716 A1 | 12/2013 | Vanderpohl, III | |
| 2014/0059780 A1 | 3/2014 | Lafleche et al. | |
| 2014/0059781 A1 | 3/2014 | Lafleche et al. | |
| 2014/0076644 A1 | 3/2014 | Derenne et al. | |
| 2014/0080413 A1 | 3/2014 | Hayes et al. | |
| 2014/0266733 A1 | 9/2014 | Hayes et al. | |
| 2014/0343639 A1 | 11/2014 | Hopper et al. | |

OTHER PUBLICATIONS

International Written Opinion for PCT/US2015/015889, the international counterpart to U.S. Appl. No. 14/622,221.

\* cited by examiner

COMMUNICATION METHODS FOR PATIENT HANDLING DEVICES

CROSS-REFERENCE TO RELATED APPLICATIONS

This application claims priority to U.S. provisional patent application Ser. No. 61/940,092 filed Feb. 14, 2014 by inventors Krishna Bhimavarapu et al. and entitled COMMUNICATION METHODS FOR A PATIENT HANDLING DEVICE, the complete disclosure of which is incorporated herein by reference.

BACKGROUND OF THE INVENTION

The present invention relates to person support apparatuses, such as, but not limited to, beds, stretchers, chairs, recliners, operating tables, and cots. The present invention also relates to patient care devices, such as, but not limited to, patient thermal control systems.

SUMMARY OF THE INVENTION

Patient care devices and patient support apparatuses according to one aspect of the invention include communication systems that provide an improved architecture for efficiently handling internal communication amongst nodes and/or external communication with one or more external nodes. Some aspects of the improved architecture include faster communication, the ability to partially share communication channels with external devices, a reduction in set-up time, easier re-configurability and/or implementation of software/firmware updates, added security, improved diagnostics, and/or greater functionality.

According to one aspect of the invention, a person support apparatus is provided that includes a support surface, first and second modules, and first and second communication networks. The support surface is adapted to support a person. The first module is adapted to perform a first function associated with the person support apparatus, and the second module is adapted to perform a second function associated with the person support apparatus. The first communication network is coupled to the first and second modules and is adapted to transport data between the first and second modules using a first communication protocol. The second communication network is also coupled to the first and second modules and is adapted to transport data between the first and second modules using a second communication protocol. The second communication protocol is different from the first communication protocol.

According to another aspect, a person support apparatus is provided that includes a support surface, first and second modules, and first and second communication networks. The support surface is adapted to support a person. The first module is adapted to perform a first function associated with the person support apparatus. The second module is adapted to perform a second function associated with the person support apparatus. The first communication network is coupled to the first and second modules, and the second communication network is also coupled to the first and second modules. The first module transmits a first command to the second module over both the first and second communication networks, and the second module is adapted to follow the first command if the second module receives the first command from the second communication network but does not receive the first command from the first communication network.

According to still another aspect, a person support apparatus is provided that includes a frame, a support surface, a plurality of siderails, a first module, a second module, a third module, and a network switch. The support surface is supported by the frame and is adapted to support a person. The siderails are movable between a lowered position and a raised position. The first module is adapted to perform a first function associated with the person support apparatus and the first module has a first address. The second module is adapted to perform a second function associated with the person support apparatus and the second module has a second address. The third module is adapted to perform a third function associated with the person support apparatus and the third module has a third address. The network switch includes first, second, and third ports that are communicatively coupled to the first, second, and third modules, respectively. The network switch is adapted to automatically associate the first address to the first port based upon messages received at the first port, automatically associate the second address to the second port based upon messages received at the second port, and automatically associate the third address to the third port based upon message received at the third port.

According to other aspects, the first communication protocol is an Ethernet protocol, and the second communication protocol is one of the following: an RS-485 protocol, a serial peripheral interface (SPI) protocol, an RS-232 protocol, an RS-422 protocol, and an I-squared C protocol ($I^2C$).

In some embodiments, the first communication network transports video data and the second communication network transports commands for moving at least one component of the person support apparatus.

The first function includes displaying graphics on a display of the person support apparatus, the second function includes controlling movement of the support surface, and the third function includes communicating with a device physically separate from the person support apparatus, in some embodiments.

In other embodiments, the person support apparatus further includes a fourth module adapted to perform a fourth function associated with the person support apparatus, the fourth module is coupled to the first, second, and third modules by the first communication network. In some embodiments, the fourth function includes driving a wheel coupled to the person support apparatus.

The first module includes a first microcontroller, the second module includes a second microcontroller, and the first microcontroller is adapted to decide whether to transmit a first message to the second module using the first communication network or the second communication network, in at least one embodiment. The first microcontroller decides whether to transmit the first message using the first communication network of the second communication network based upon the content of the first message.

In some embodiments, the first module includes a first media access control (MAC) address and a first Internet Protocol (IP) address, the second module includes a second media access control (MAC) address and a second Internet Protocol (IP) address, and the first module is adapted to communicate with the second module over the first communication network by sending messages that include both the first and second MAC addresses and both the first and second IP addresses.

In at least one embodiment, the person support apparatus is a bed, the first module is physically coupled to a frame of the bed, and the second module is physically positioned inside of a mattress positioned on top of the bed. In another embodiment, the person support apparatus is a bed having a support deck adapted to support a patient thereon, the first module is adapted to control movement of the support deck, and the second module is adapted to control movement of a drive wheel used to power movement of the bed from one location to another.

In some embodiments, the second module is adapted to not follow the first command if the second module receives the first command from the first communication network but does not receive the first command from the second communication network. The second module may be adapted to follow the first command if the second module receives the first command from both the first and second communication networks. The first command, in some embodiments, instructs the second module to physically move a component of the person support apparatus.

In still other embodiments, the person support apparatus is a bed, the first module is physically coupled to a frame of the bed and includes a serializer/deserializer output for transmitting image data to a display mounted on a footboard of the bed, wherein the image data transmitted to the display is generated from a scalable vector graphics (SVG) format. The first module receives a size message from the display indicative of a physical size of the display, wherein the first module adjusts the image data transmitted by the first module to the display based upon the size message. Different footboards may thereby be coupled to the bed having different sized displays without requiring reprogramming of the first module.

The first, second, and third addresses are media access control (MAC) addresses in some embodiments, and the network switch is adapted to automatically associate Internet Protocol (IP) addresses with the MAC addresses. The modules communicate with each other over the communication network using the TCP/IP protocol suite, in at least one embodiment.

The person support apparatus also includes, in at least one embodiment, a communication bus coupled between the first, second, and third modules, and the communication bus carries messages between the first, second, and third modules without passing through the network switch.

In some embodiments, the second module includes a WiFi transceiver adapted to communicate with a wireless access point of a computer network, and the second module includes a microcontroller programmed to control motion of at least one component of the person support apparatus.

The first and second modules may be part of a first virtual local area network on the person support apparatus and the third module may be part of a second virtual local area network on the person support apparatus. In some such embodiments, the third module is physically contained within a mattress positioned on the person support apparatus.

According to another aspect, a person support apparatus is provided that includes a support surface, a first module, a second module, a third module, a communication network, and a firewall. The first, second, and third modules are each adapted to perform first, second, and third functions, respectively, that are associated with the person support apparatus. The communication network is coupled to the first, second, and third modules and is adapted to transmit packets between the first, second, and third modules. The firewall is adapted to prevent selected packets from the second module from being communicating to the third module over the communication network.

In other aspects, the second module includes an external port adapted to allow a device separate from the person support apparatus to be communicatively coupled to the first module. The selected packets originate from this device.

In some embodiments, the third function includes controlling movement of at least one component of the person support apparatus, and the first function includes displaying information on a display of the person support apparatus. The first module may be adapted to display information on the display that is received from the device via the communication network.

The first module is adapted to forward the selected packets to a wireless transceiver in communication with an external network, in at least some embodiments. The forwarding of the selected packets to the wireless transceiver enables the device to communicate with the external network.

According to another embodiment of the invention, a person support apparatus is provided that includes a support surface, first and second modules, an Ethernet connection, and a firewall. The first module is adapted to control movement of at least one component of the person support apparatus. The second includes an external port adapted to allow an external device separate from the person support apparatus to be communicatively coupled to the second module such that the second module receives selected packets from the external device via the external port. The Ethernet connection is coupled to the first and second modules, and the firewall prevents the selected packets received by the second module from being used by the first module to control movement of the at least one component of the person support apparatus.

According to other aspects, the person support apparatus further includes a third module adapted to display graphical information on a display mounted on the person support apparatus, wherein the firewall allows the selected packets to be communicated from the second module to the third module over the Ethernet connection. In some embodiments, the graphical information displayed on the display includes first data that originates from the first module and second data that originates from the selected device. The second data includes both content data that is to be displayed and visual format data (e.g. an identification of the pixels to be displayed) that defines how the content data is to be displayed on the display, in at least one embodiment. The first data does not include visual format data, and the third module determines how the first data is to be displayed on the display.

In other aspects, the display is a touch screen and the third module is adapted to transmit touch data back to the external device, the touch data identifying where a user touched the touch screen.

An Ethernet switch is coupled between the first and second modules in some embodiments.

A wireless transceiver is also included in some embodiments that is adapted to communicate with an external network. The second module forwards the selected packets to the wireless transceiver in order to enable the external device to communicate with the external network.

According to another embodiment of the invention, a person support apparatus is provided that includes a base, a frame, a support surface, a plurality of siderails, first and second modules, a communication network, and a port. The frame is supported on the base and the support surface is supported on the frame. The siderails are supported by the frame and are movable between a lowered position and a raised position. The first module performs a first function associated with the person support apparatus and includes a first web server. The second module performs a second function associated with the person support apparatus and includes a second web server. The communication network is coupled to the first and second modules. The port allows an external device to be communicatively coupled to the communication network and to access the first and second web servers.

In some embodiments, first and second web servers serve web pages containing diagnostic information about the first and second modules, respectively.

In at least one embodiment, the first function includes controlling a height of the support surface relative to the base. The second function includes controlling a display on the person support apparatus, in some embodiments.

The display may be a touch screen display.

According to another embodiment of the invention, a person support apparatus is provided that includes a base, a frame, a support surface, a plurality of siderails, first and second modules, and a communication network. The frame is supported on the base and the support surface is supported on the frame. The siderails are supported by the frame and are movable between a lowered position and a raised position. The first module controls movement of the support surface and the second module controls a display on the person support apparatus. The communication network is coupled to the first and second modules, and the first module transmits to the second module image data that specifies at least one image that is to be displayed on the display.

According to other aspects, the second module is also adapted to display at least one second image on the display, and the second module is adapted to specify a format of the second image on the display. The format of the second image is not defined from data transmitted by the first module to the second module. In some embodiments, the second module is adapted to simultaneously display on the display both the image and the second image, while in other embodiments, the second module is adapted to toggle between displaying the image and the second image on the display. Still further, in at least one embodiment, the display includes a touch screen and the toggling is controlled by a user touching a region of the touch screen.

The image data is transmitted as a bitmap file, a jpeg (Joint Photographics Experts Group) file, a scalable vector graphics files, or another type of image file.

According to other aspects, the first module transmits multiple images to the second module that are displayed sequentially by the second module on the display in order to create moving graphics on the display. The content of the moving graphics is based upon data received by the first module from one or more sensors, in at least one embodiment.

In other embodiments, the person support apparatus includes a third module coupled to the communication network, wherein the third module transmits to the second module third image data that specifies at least one third image that is to be displayed on the display. The second module may be adapted to simultaneously display on the display the image, the second image, and the third image; or, in other embodiments, the second module is adapted to toggle between displaying the image, the second image, and the third image on the display. Such toggling may be controlled via by a user touching a region of a touch screen. The third module may transmit multiple images to the second module that are displayed sequentially by the second module on the display in order to create moving graphics on the display.

According to another embodiment, a person support apparatus is provided that includes a base; a frame supported on the base; a support surface supported on the frame and adapted to support a person; a plurality of siderails movable between a lowered position and a raised position; first, second, and third modules; a communication network, and a dynamic host configuration protocol (DHCP). The first, second, and third modules are adapted to perform first, second, and third functions, respectively, that are associated with the person support apparatus. The communication network is coupled to the first, second, and third modules. The DHCP server is contained with the first module, and the second and third modules are configured to request IP addresses from the DHCP server.

According to other aspects, the DHCP server leases IP addresses to the second and third modules that are used by the second and third modules for communicating over the communication network. In some embodiments, the length of the lease is varied depending upon whether the requesting module is original equipment of the bed or an add-on. In other embodiments, the communication network is adapted to communicate with a fourth module that is external to the person support apparatus, and the length of the lease granted by the DHCP server to the fourth module is different from the length of the lease granted by the DHCP server to at least one of the second and third modules.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
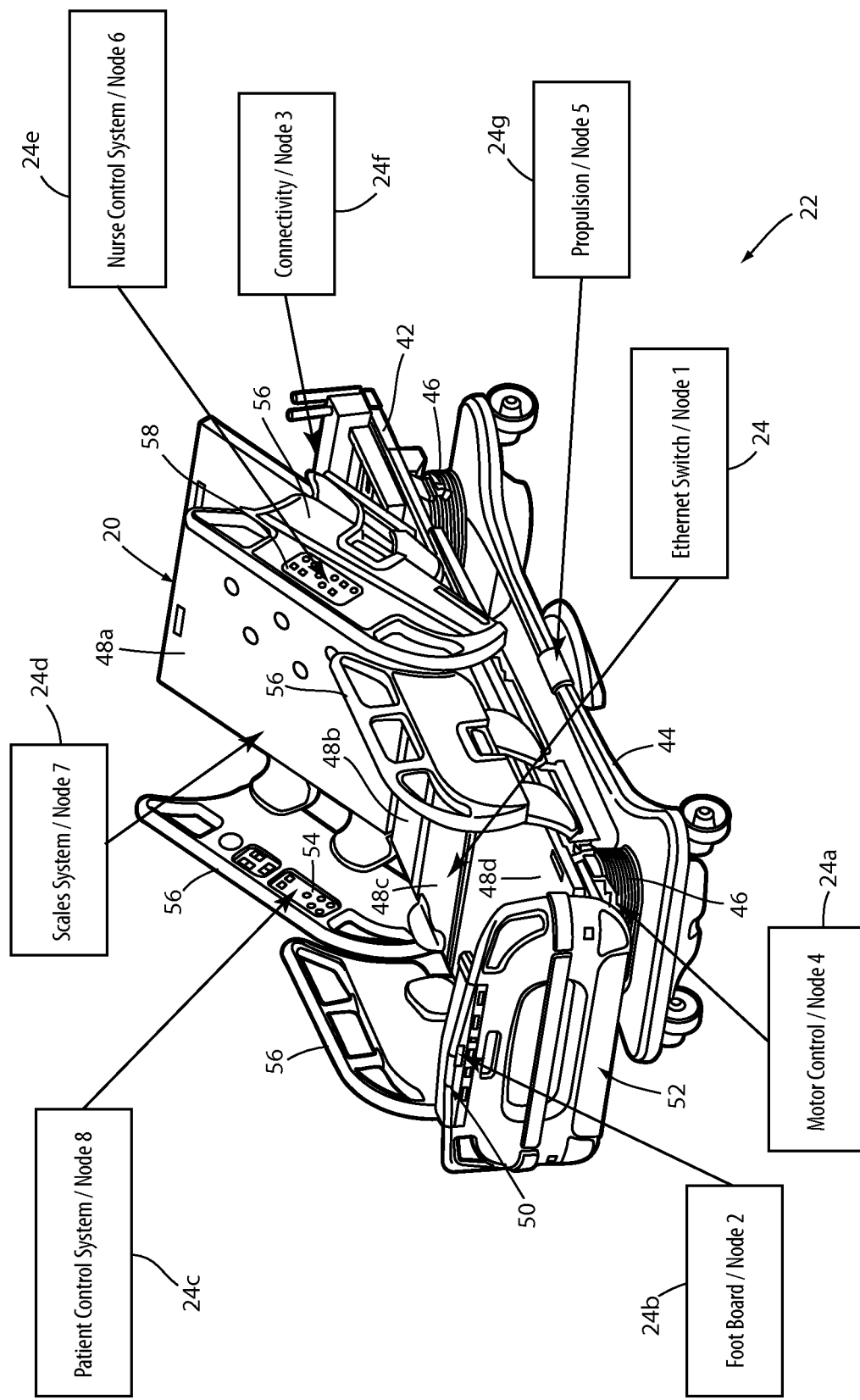
FIG. 1 is a perspective view of one example of a person support apparatus according to one embodiment.
Figure 7:
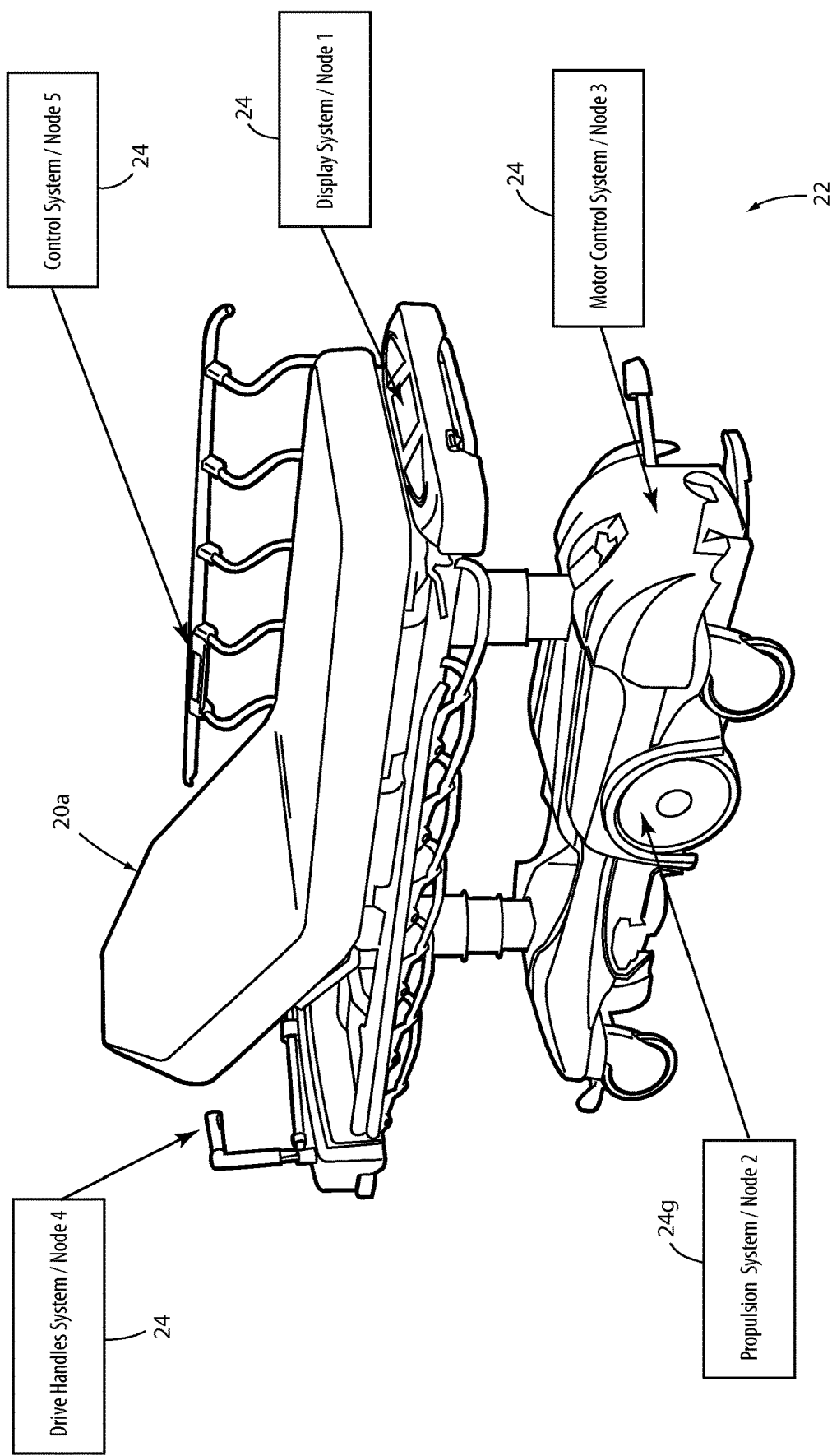
FIG. 7 is a perspective view of another person support apparatus incorporating aspects of the communication systems disclosed herein.
Figure 8:
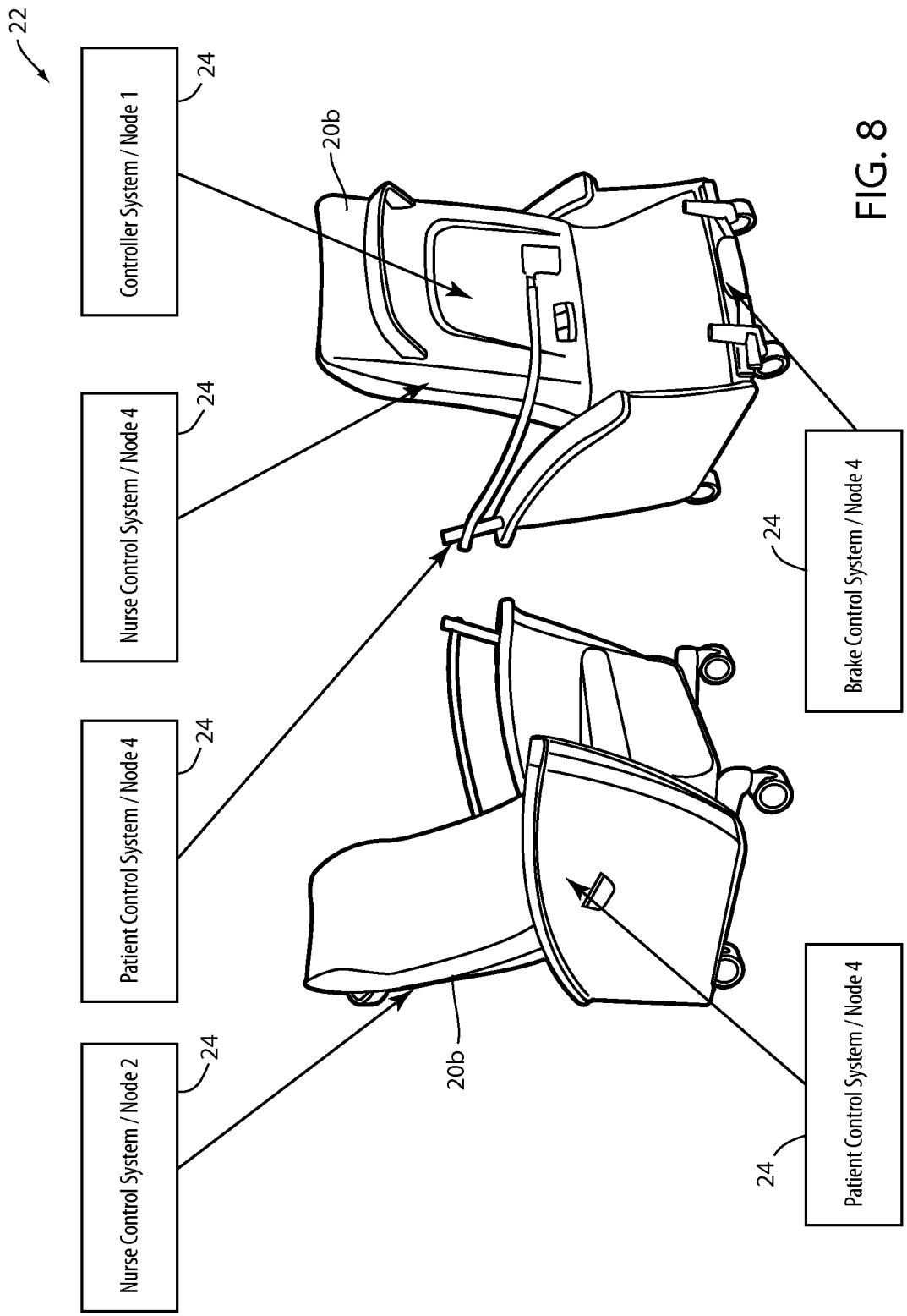
FIG. 8 is a front and rear perspective view of yet another person support apparatus incorporating aspects of the communications systems disclosed herein.
Figure 9:
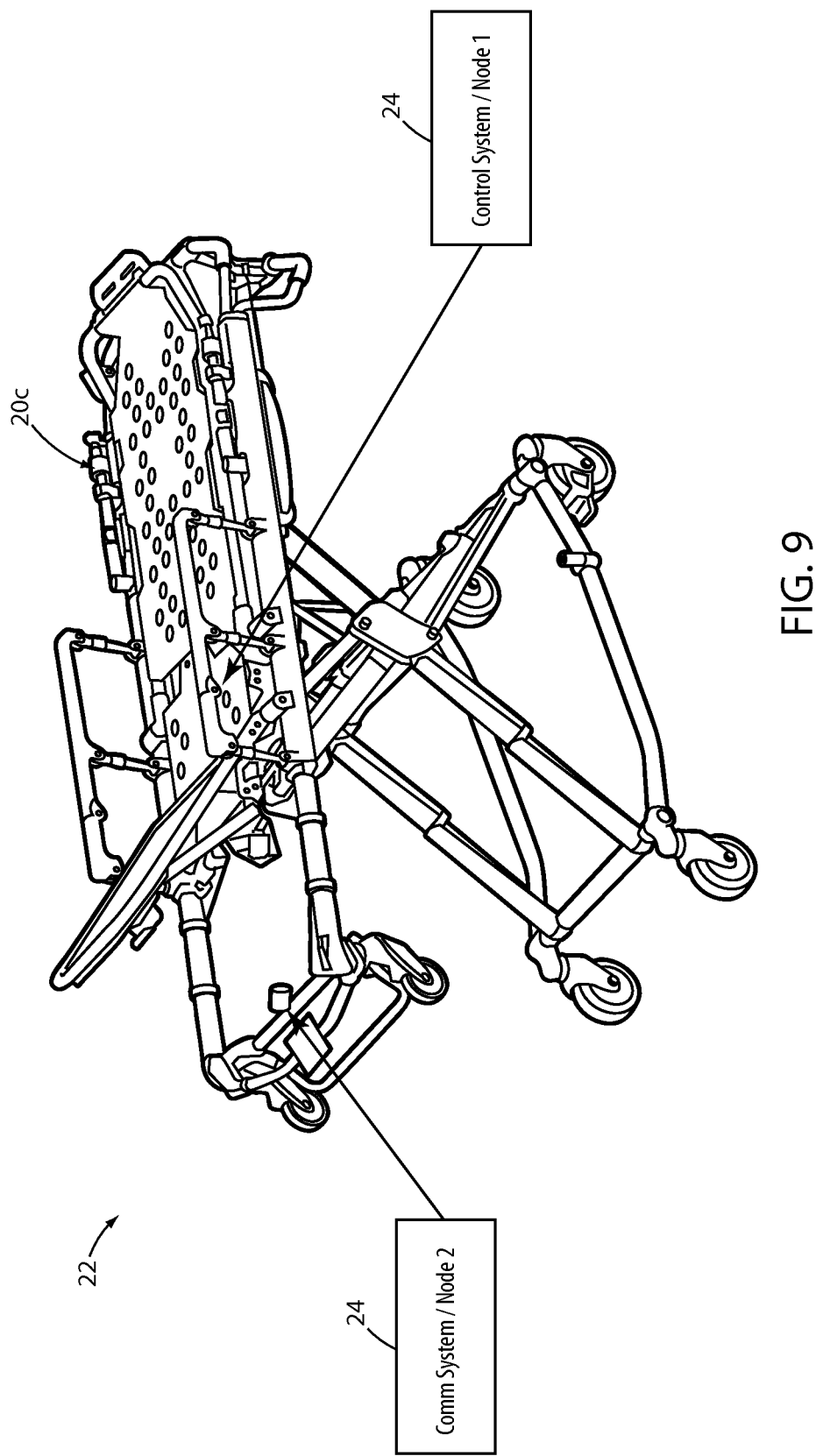
FIG. 9 is a perspective view of yet another person support apparatus incorporating aspects of the communication systems disclosed herein.
Figure 10:
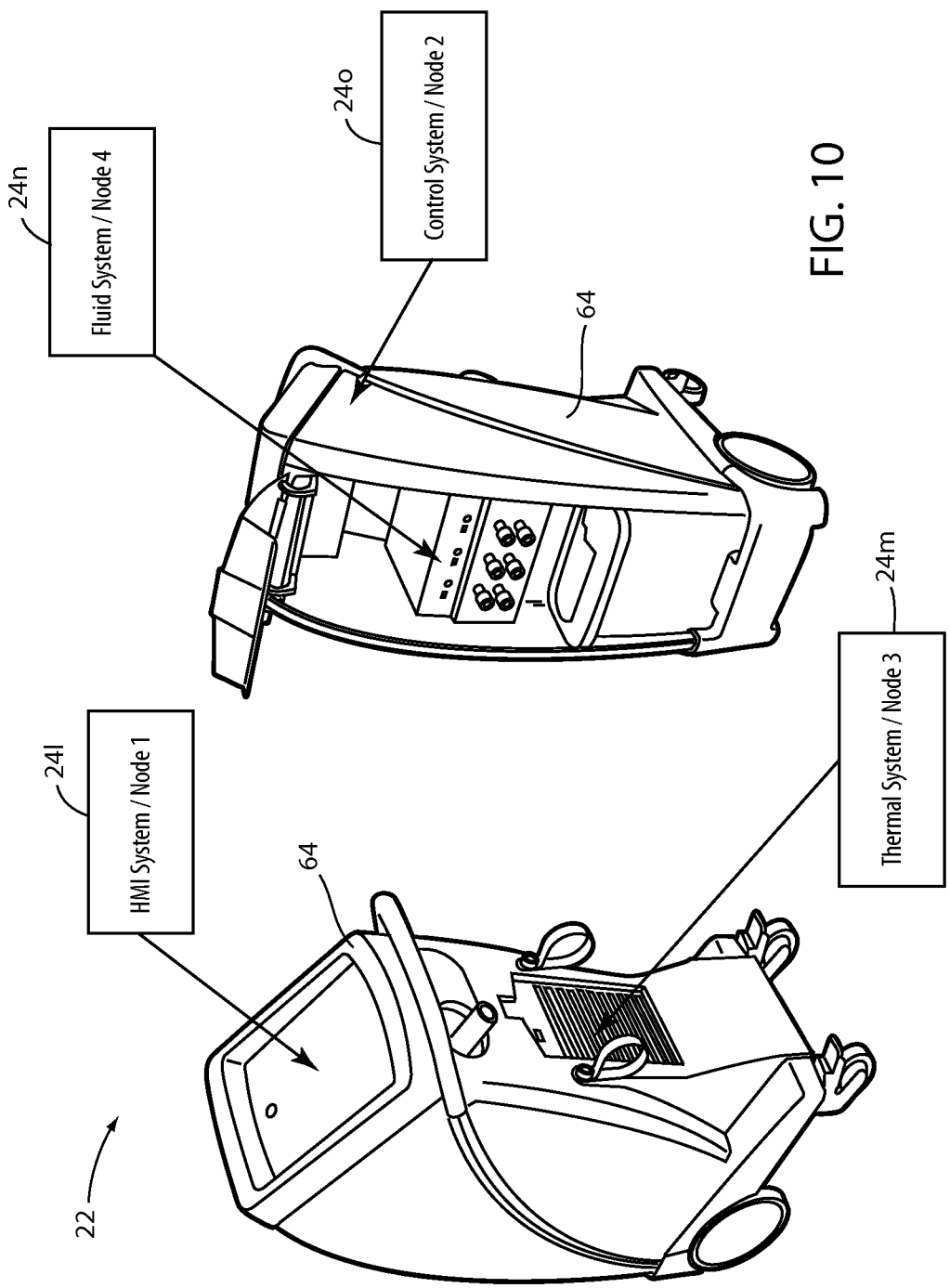
FIG. 10 is a front and rear perspective view of a patient temperature control system incorporating aspects of the communication system disclosed herein.
Figure 11:
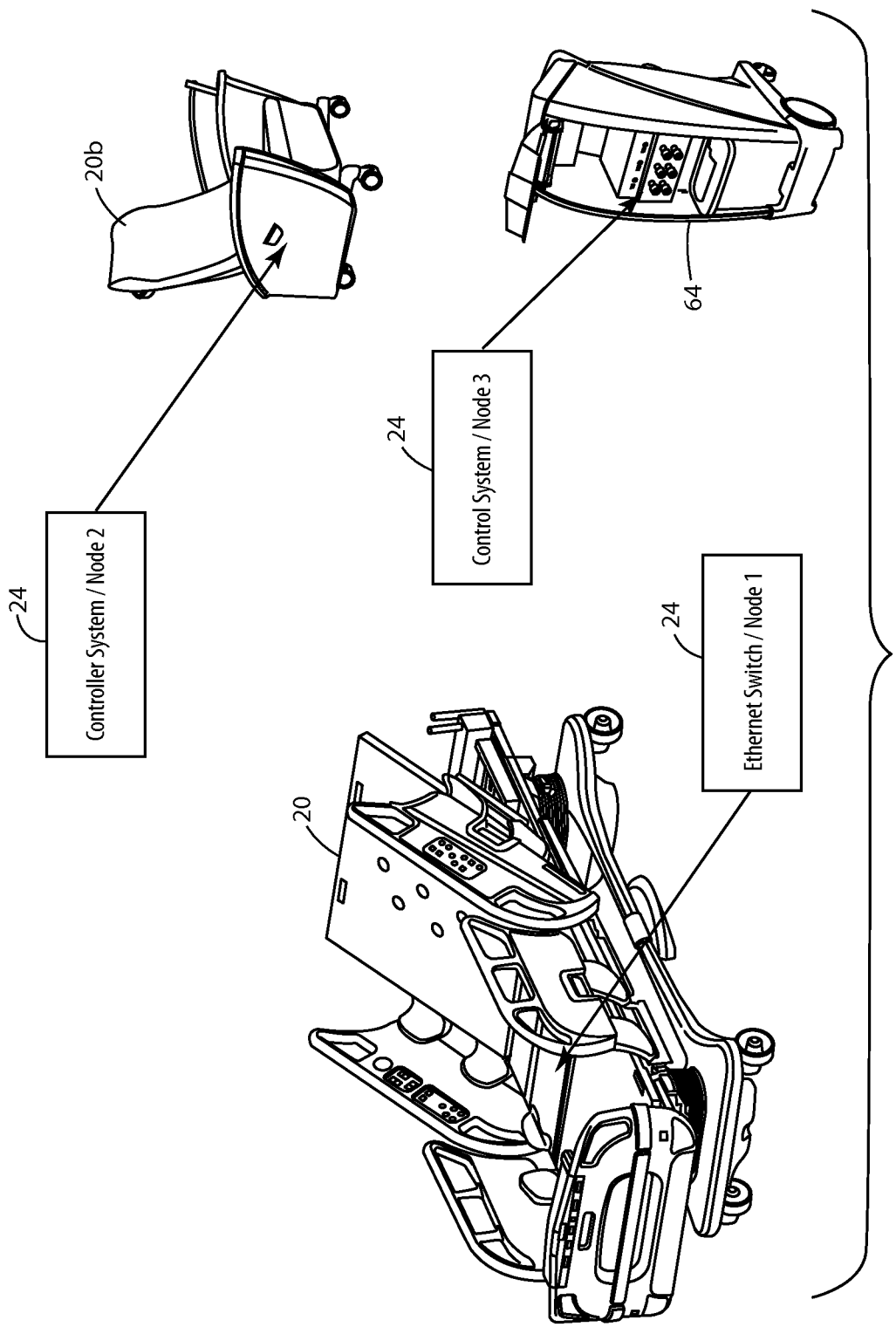
FIG. 11 is a perspective view of a plurality of medical devices incorporating aspects of the communication systems disclosed herein.

FIG. 1 illustrates a person support apparatus 20 that includes an improved communications system 22 according to one embodiment. In the embodiment illustrated in FIG. 1, person support apparatus 20 is a bed. It will be understood, however, that person support apparatus 20 can take on a variety of other forms besides a bed. For example, FIGS. 7-9 illustrate person support apparatuses 20 in the form of a stretcher, recliner, and cot, respectively. Still other forms of person support apparatuses can be used. As shown in FIG. 10, communication system 22 can also be incorporated into a patient thermal control unit 64. Still further, as shown in FIG. 11 communication system 22 can also be incorporated across multiple devices, such as the person support apparatuses 20, 20b, and thermal control unit 64 shown in FIG. 11. Still other variations and embodiments of communication system 22 are possible.

Person support apparatus 20 (FIG. 1) includes a communications system 22 having a communication network (not labeled in FIG. 1) that includes a plurality of electronic nodes or modules 24 that are adapted to communicate with each other. In the particular embodiment of FIG. 1, which is merely illustrative of the various manners in which communication system 22 can be configured, system 22 includes seven modules 24 and one Ethernet switch 28, which may itself be configured as a module 24, in at least some embodiments. Modules 24 communicate with each other in a peer-to-peer fashion over an Ethernet 26, in at least one embodiment. Modules 24 further communicate over a lower speed network 84 (described below). The communication over Ethernet 26 and network 84 uses error checking and correcting (CRC, Checksum, etc.), packetization, prioritization, collision detection and avoidance, and provides improved resistance to, and reliability against, electrostatic discharges (ESD). In some embodiments, modules 24 send and/or receive variable sized packets in the data transport layer.

As will be described in greater detail below, modules 24 include electronic circuit boards that assist in one or more of the following: controlling internal motion of various devices (pumps, motors and actuators); displaying information from the various devices or neighboring devices; providing user interfaces for input by users; measuring weights with an on-board scale system; communicating with a healthcare facility's network including its nurse call system; driving a device within the hospital environment by use of a manual user input, such as drive handles, or by receiving input via one or more load cells or strain gages; receiving feedback or other sensor information from various devices using sensors, such as, but not limited to, Hall effect sensors; and receiving and transmitting data from sensors to displays, from displays to data aggregators, from aggregators to wireless devices and from displays to command and control devices.

A motion control module 24a (FIGS. 1, 3-5) is adapted to control movement of various components of person support apparatus 20, such as, but not limited to, the up/down movement of a litter frame 42 whose height is adjustable with respect to a base 44 by way of a pair of height adjusters 46. Motion control module 24a may also control pivoting of various sections 48 of a deck that is supported on litter frame 42. As shown in FIG. 1, person support apparatus 20 includes a head section 48a, a seat section 48b, a thigh section 48c, and a foot section 48d. Motion control module 24a controls, in at least some embodiments, pivoting of head section 48a about a first substantially horizontal axis, pivoting of thigh section 48c about a second substantially horizontal pivot axis, and pivoting of foot section 48d about a third substantially horizontal pivot axis.

A footboard module 24b, in at least one embodiment, controls a user interface 50 positioned on a footboard 52 of person support apparatus 20. User interface 50, in at least some embodiments, includes a plurality of buttons for activating and deactivating the motors that are controlled by motion control module 24a. User interface 50 also includes one or more displays, at least one of which is a touchscreen, in at least one embodiment. In addition to controlling movement of person support apparatus 20, user interface 50 also allows a user to take weight measurements of a person supported on support apparatus 20, configure alert settings, and control other aspects of person support apparatus 20.

A patient siderail module 24c, in at least one embodiment, controls a patient user interface 54 positioned on an interior side of a siderail 56. Patient user interface 54 enables a patient, or other individual, who is lying or sitting on person support apparatus 20 to control various aspects of person support apparatus 20, such as, but not limited to, the up/down movement of litter 42, the pivoting of various of the deck sections 48, the contacting of—and communication with—a remotely positioned nurse, and the control of one or more environmental features (e.g. volume and/or channel of a nearby television, etc.).

A scale module 24d, in at least one embodiment, controls a scale system that is integrated into person support apparatus 20. Such a scale system includes, in at least one embodiment, four load cells that are positioned generally near, and under, each corner of litter 42. The load cells sense the amount of downward weight that is exerted by a patient, or other occupant, of person support apparatus 20. In at least one embodiment, the load cells are constructed and configured to operate in the manners disclosed in commonly assigned U.S. Pat. No. 5,276,432 issued to Travis and entitled PATIENT EXIT DETECTION MECHANISM FOR HOSPITAL BED. In addition to providing a scale function for weighing an occupant of person support apparatus 20, scale module 24d, in at least one embodiment, analyzes the outputs of the load cells to also provide an exit detection function whereby local and/or remote alerts are issued—when the exit detection feature is armed—and the occupant attempts to exit, and/or fully succeeds in exiting, person support apparatus 20.

A nurse siderail control module 24e, in at least one embodiment, controls a caregiver user interface 58 positioned on an exterior side of a siderail 56. Caregiver user interface 58 enables a caregiver, or other person standing adjacent to person support apparatus 20, to control various aspects of person support apparatus 20, such as, but not limited to, the up/down movement of litter 42 and the pivoting of various of the deck sections 48. In addition, caregiver user interface 58 may include controls for activating and deactivating one or more of the following: a brake of person support apparatus 20, an exit detection system incorporated into person support apparatus 20, and/or one or more lockouts that lock out selected controls of patient user interface 54.

A connectively module 24f, in at least one embodiment, controls communication between person support apparatus 20 and one or more devices that are located off-board of person support apparatus 20. Connectivity module 24f thus acts as a gateway between the on-board communication system 22 and one or more external devices off-board person support apparatus 20. In many embodiments, connectivity module 24f provides a communication port for a nurse call cable that connects to a conventional nurse call outlet in the headwall of a hospital. Connectivity module 24f, in at least one embodiment, also includes one or more wireless transceivers for wirelessly communicating with one or more external structures, as will be described in greater detail below. In at least one embodiment, connectivity module 24f includes a WiFi transceiver (IEEE 802.11) that enables wireless communication between person support apparatus 20 and one or more wireless access points of a local area network, such as, but not limited to, a hospital Ethernet.

A propulsion control module 24g, in at least one embodiment, controls an on-board propulsion system that drives one or more wheels of person support apparatus 20, thereby easing the physical load otherwise experienced by a caregiver when moving person support apparatus 20 from one location to another. In at least one embodiment, the on-board propulsion system is constructed and configured in any of the manners disclosed in commonly assigned U.S. patent application Ser. No. 13/795,193, filed Mar. 12, 2013 by inventors Richard Derenne et al. and entitled POWERED PATIENT SUPPORT APPARATUS, and/or in U.S. Pat. No. 6,772,850 issued to Waters et al. and entitled POWER ASSISTED WHEELED CARRIAGE, the complete disclosures of both of which are hereby incorporated herein by reference. Other types of on-board propulsion systems may also be used.

Ethernet switch 28, which may comprise its own separate module 24, or which may be integrated into any one or more of the other modules 24a-g, communicatively couples together the various modules 24 so that they are able to communicate with each other using an Ethernet protocol. In other embodiments, as will be discussed in greater detail below, one or more of modules 24 may also communicate with each other using a separate and different communication network.

Figure 2:
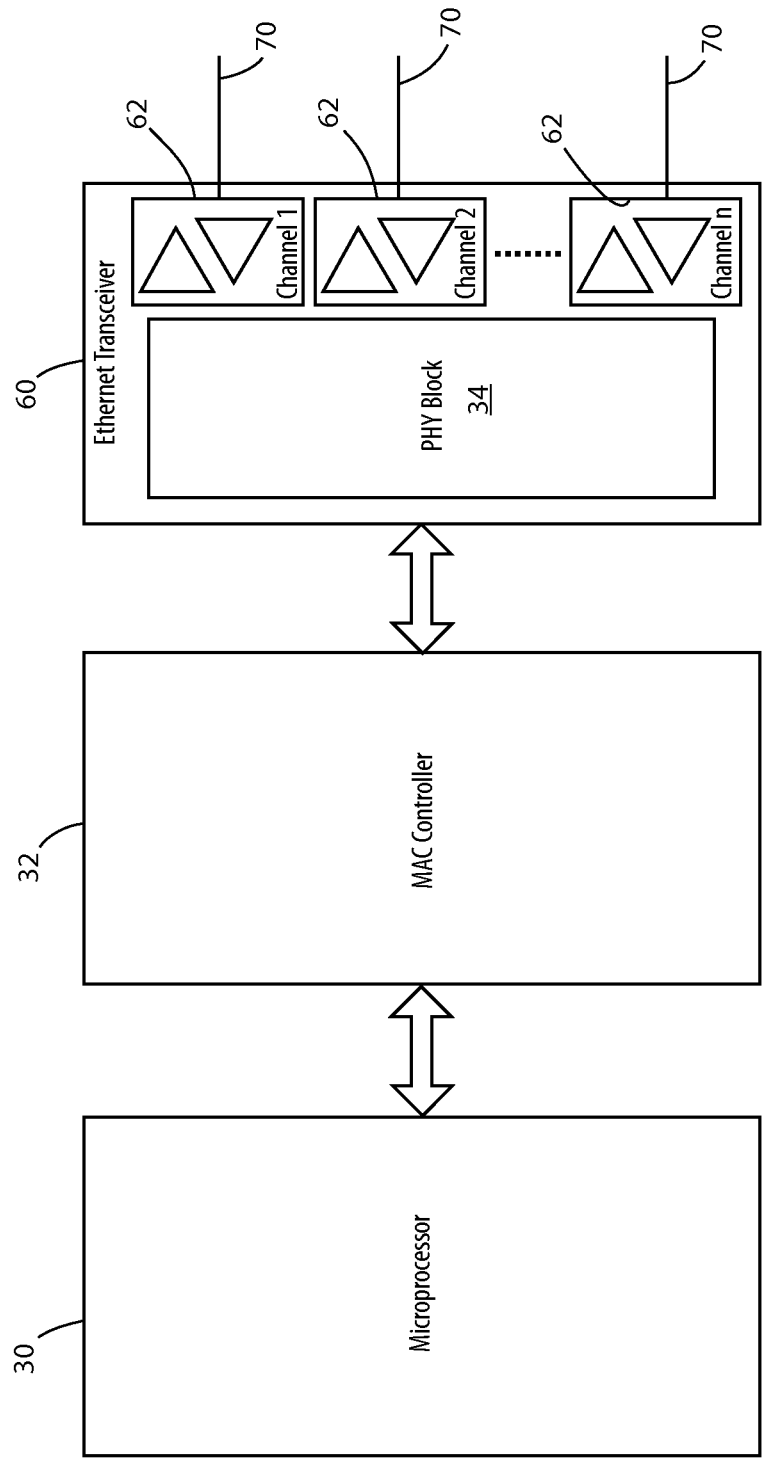
FIG. 2 is a block diagram of an example of a node or module that is usable in the various communication systems described herein.

As shown in more detail in FIG. 2, each module 24 includes a conventional microprocessor and/or microcontroller 30 and at least one network transceiver 60 that enables each of the modules to talk to each other. In some embodiments, the network transceiver 60 includes multiple input/output (I/O) ports 62 that enable module 24 to communicatively couple to multiple other modules 24 or multiple other devices on Ethernet 26. Using a single port 62, modules 24 can be coupled to Ethernet switch 28 in a star topology, such as that shown in FIG. 3. By utilizing multiple ports 62 in one or more modules 24, however, other network topologies can be implemented in one or more of the embodiments disclosed herein, including ring topologies, combinations of ring and star topologies, and still others.

The ports 62 are adapted to physically couple to whatever physical media is used to form one or more communication links 70 between the modules 24 of the Ethernet 26. In one embodiment, the physical media used to implement each link 70 of the Ethernet 26 is twisted pair copper wire. In another embodiment, the physical media used to implement each link 70 of the Ethernet 26 is fiber optic cables. In still other embodiments, Ethernet 26 includes some links 70 that are defined by a first physical media (e.g. twisted pair copper wire, fiber optic cables, etc.) and some other links 70 that are defined by a second physical media that is different from the first physical media. Still further, in some embodiments, the data transmission rates over links 70 are not uniform across all links 70. For example, in some embodiments, some links 70 are configured as 10 BASE-T while other links are configured as 100 BASE-T. In at least one such embodiment, the link 70 between propulsion module 24g and switch 28 is 10 BASE-T while the other links 70 are 100 BASE-T and/or higher speed links. In some embodiments, one or more of the links 70 are any of the various gigabit Ethernet variants (e.g. 1000 BASE-T, 1000 BASE-SX, 1000 BASE-SX, etc.), ten gigabit Ethernet variants (e.g. 10 GBASE-SR, 10 GBASE-LX4, etc.), forty gigabit Ethernet variants (e.g. 40 GBASE-KR4, 40 GBASE-CR4, etc.), and/or terabit Ethernet variants.

Figure 3:
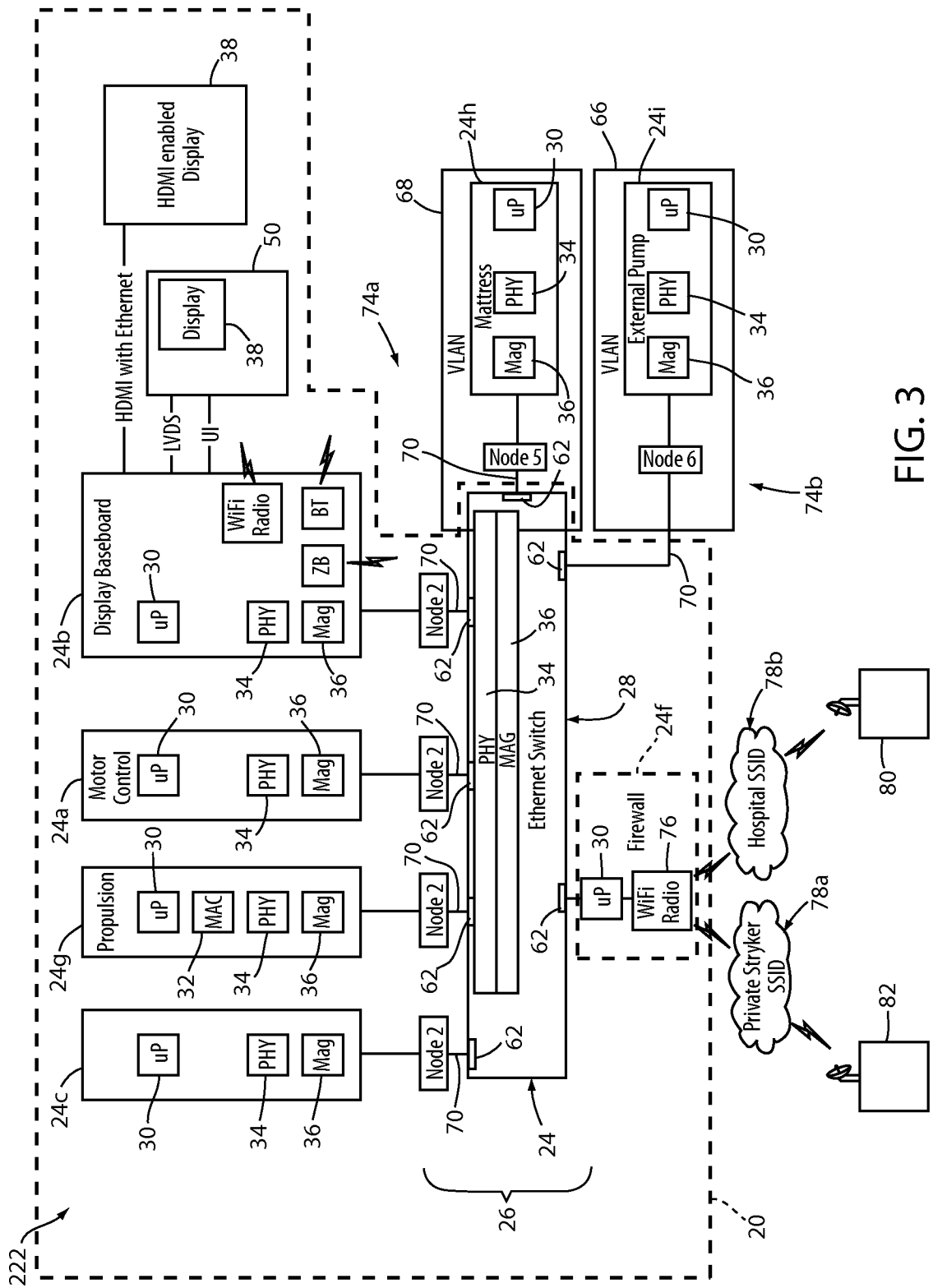
FIG. 3 is a block diagram of an embodiment of a communication system that is usable in the person support apparatus of FIG. 1, or any of the other support apparatuses or devices described herein.

FIG. 3 illustrates an alternative embodiment of a communication system 222 that can be included in one or more of the person support apparatuses 20 and/or thermal control units 64 described herein. Those components of communication system 222 that are the same as communication system 22 are labeled with the same reference numbers and operate in the same manner as previously described, unless explicitly stated otherwise. Those components of system 222 that are not found in system 22 are provided with a new reference number and their construction and operation is described in more detail below.

As shown in FIG. 3, communication system 222 includes multiple nodes or modules 24 that communicate over an Ethernet 26 that includes at least one Ethernet switch 28 adapted to interchange data between the nodes or modules 24. One or more microprocessors/microcontrollers 30 having internal or external MAC devices 32 communicate using Ethernet physical layer transceivers (PHY transceivers) 34 and Ethernet magnetics 36 included within each module 24. Multiple modules 24 connected together to Ethernet switch 28 make up Ethernet 26. Ethernet switch 28 itself contains a PHY transceiver 34 and magnetics 36. The PHY transceiver connects the link layer MAC devices 32 to the physical layer (e.g. links 70 discussed below). The magnetics provide galvanic isolation between the modules 24 and the physical layer links 70.

The PHY transceiver 34 and magnetic blocks 36 of switch 28 are used to couple the module 24 to one or more links 70 that, in turn, are coupled to one or more modules 24 and/or one or more Ethernet switches 28. More specifically, switch 28 includes a plurality of ports 62 into which cables, or other physical media, are insertable in order to establish communication links 70 between switch 28 and nodes 24. In different embodiments, ports 62 are Registered Jack 45 (RJ-45) connectors, Augmented Registered Jack 45 (ARJ45) connectors (HS, HD, and/or others), GigaGate 45 (GG45) connectors, and/or other types of connectors.

The modules 24 of communication network 222 include footboard module 24b, propulsion module 24g, connectivity module 24f, a mattress module 24h, and an external device module 24i, which is illustrated in FIG. 3 as being specifically for an external pump 66, but can be used for other external devices. Modules 24*b, g*, and *f* were previously described above. Modules 24*h* and 24*i* are described in more detail below.

Mattress module 24*f*, in at least one embodiment, controls various aspects of a powered mattress 68. Powered mattress 68 is an inflatable mattress that contains multiple air bladders whose inflation and deflation levels are controlled by mattress module 24*h*. In some embodiments, powered mattress 68 is any one of the mattresses sold under the brand names Revive and/or XPRT by Stryker Corporation of Kalamazoo, Mich. In some embodiments, powered mattress 68 includes any one or more of the features described in commonly assigned U.S. patent application Ser. No. 13/836,813 filed Mar. 15, 2013 by inventors Patrick Lafleche et al. and entitled INFLATABLE MATTRESS AND CONTROL METHODS and/or commonly assigned U.S. patent application Ser. No. 14/308,131 filed Jun. 18, 2014 by inventors Patrick Lafleche et al. and entitled PATIENT SUPPORT COVER, the complete disclosures of both of which are incorporated herein by reference. In still other embodiments, still other types of mattresses 68 may be used.

Mattress module 24*f*, like modules 24*a, b, f, g*, and *i*, is communicatively coupled to Ethernet switch 28 by a communication link 70. Mattress module 24*h* transmits status and other message to footboard module 24*b* over link 70 that provide an indication of the current state of one or more aspects of mattress 68, such as, but not limited to, the current inflation pressure of one or more sections of mattress 68, the state of any therapies that are currently being provided by mattress 68, and/or other information about mattress 68. Some of that information is selectively displayed by footboard module 24*b* on one or more displays 38 that are in communication with footboard module 24*b*.

One such display 38, as shown in FIG. 3, is incorporated into a footboard user interface 50 that is mounted to an upper portion of footboard 52. Another display 38 is coupled to footboard module 24*b* by way of a High Definition Multimedia Interface (HDMI) connection 72. In other embodiments, this second display is coupled to footboard module 24*b* by way of a different type of video interface, such as, but not limited to, the Digital Visual Interface (DVI) developed by the Digital Display Working Group, a Video Graphics Array (VGA) interface, a Plug and Display (P&D) interface, a Digital Flat Panel (DFP) interface, any type of interface that utilizes the EIC/CEA-861 standards, or still other types of interfaces.

This second display can be mounted to an upper portion of footboard 52, or it can be positioned elsewhere. Either or both of the displays 38 are, in at least one embodiment, touch screens that include icons or other images that, when touched, allow a user to control various aspects of person support apparatus 20 and/or mattress 68. Thus, in at least one embodiment where one or more displays 38 are configured as touch screens, displays 38 sense when a user has touched specific areas of the display 38 and relay that information back to footboard module 24*b*. Footboard module 24*b*, in turn, sends messages to mattress module 24*h* that identify what areas of the touch screen have been touched, or what controls have been pressed by the user. These messages are sent from footboard module 24*b* over link 70 to Ethernet switch 28 which then forwards the message to mattress module 24*h*. In response to these messages, mattress module 24*h* takes appropriate action in controlling mattress 68, such as, for example, inflating or deflating one or more sections of mattress 68, starting or stopping one or more therapies implemented by mattress 68, and/or taking other actions.

In some embodiments, footboard module 24*b* is in communication with one or more buttons, or other controls that can be used to control one or more aspects of mattress 68. In those embodiments, footboard module 24*b* sends messages to mattress module 24*h* over Ethernet 26 informing mattress module 24*h* of which buttons and/or controls have been activated or deactivated by the user. In the configuration of Ethernet 26 shown in FIG. 3, such messages pass from footboard module 24*b* to switch 28 over one link 70, and then pass from switch 28 to mattress module 24*h* over another link 70.

External device module 24*i* is also communicatively coupled to Ethernet switch 28 by a communication link 70. External device module 24*i* transmits status and other message to footboard module 24*b* over links 70 that provide an indication of the current state of one or more aspects of whatever external device happens to be coupled to Ethernet 26. When the external device is a pump, such as shown in FIG. 3, such information may include vital sign information and/or any other types of information that are usefully displayed when utilizing a pump for treating a patient. Some of that information is selectively displayed by footboard module 24*b* on one or more of the displays 38 discussed above.

In some embodiments, one or more controls on user interface 50—including either of displays 38 if they are implemented as touch screens—are usable for controlling one or more aspects of the external device 66. In those instances, footboard module 24*b* sends messages to external device module 24*i* over Ethernet 26 informing external device module 24*i* of which buttons and/or controls have been activated or deactivated by the user. In the configuration of Ethernet 26 shown in FIG. 3, such messages pass from footboard module 24*b* to switch 28 over one link 70, and then pass from switch 28 to external device module 24*i* over another link 70.

In at least one embodiment of person support apparatus 20, ports 62 are provided on person support apparatus 20 at easily accessible locations for allowing a caregiver to connect and/or disconnect mattress module 24*h* and/or external device module 24*i* to the Ethernet 26 of person support apparatus 20. Such ports 62 are implemented, in at least one embodiment, as RJ-45 receptacles that are positioned at locations that are easily accessible to a user to plug in an Ethernet cable having a mating RJ-45 connector. The location may be on the footboard, or around the periphery of the litter of person support apparatus 20, or at some other location that is typically visible to a caregiver standing nearby person support apparatus 20.

In some embodiments, Ethernet switch 28 is located at a generally inaccessible location on person support apparatus 20. Such a location includes anywhere on person support apparatus 20 where one or more components of person support apparatus 20 have to be partially or wholly disassembled or removed before a person can access Ethernet switch 28. As one such example, Ethernet switch 28 is positioned in the interior of litter 42 and underneath deck sections 48. In such embodiments, two Ethernet cables run from the switch 28 to Ethernet connectors (e.g. RJ-45 connectors) that are positioned at locations that are convenient for a caregiver to plug an Ethernet cable into, such as an Ethernet cable from either mattress 68 or external device 66. This enables a caregiver to easily set up the communication channels between person support apparatus 20 and either or both of mattress 68 and external device 66 without requiring the caregiver to disassemble or remove anything on person support apparatus, or take other time consuming actions.

In at least one embodiment of person support apparatus 20, Ethernet switch 28 is configured to create a first virtual local area network (VLAN) 74a that includes mattress module 24h, footboard module 24b, and the links 70 that couple these two modules to switch 28. Ethernet switch 28 creates VLAN 74a through software, in one embodiment. In another embodiment, VLAN 74a is created via hardware. Whether implemented in hardware or software, VLAN 74a is communicatively isolated from the other modules 24 of Ethernet 26 (e.g. modules 24f, 24a, 24i, etc.). That is, mattress module 24h is not able to transmit messages or Ethernet frames to any other of the modules 24 other than footboard module 24b. (Footboard module 24b, however, is still able to communicate with all the other modules 24). Ethernet switch 28 implements VLAN 74a by routing the packets that it receives from mattress module 24h to only footboard module 24b. In other words, the packets that switch 28 receives at its port 62 that is coupled to mattress module 24h are not forwarded over any of the other links 70 to which switch 28 is coupled. Instead, they are only forwarded to footboard module 24b.

The creation of VLAN 74a facilitates the use of third party mattresses 68 in conjunction with person support apparatus 20. That is, mattresses 68 that are manufactured by companies other than the manufacturer of person support apparatus 20 can utilize user interface 50 on footboard 52 of person support apparatus for both displaying data and receiving control inputs via VLAN 74a. However, the creation of VLAN 74a ensures the manufacturer of person support apparatus 20 that the third party mattress module 24h inside of the third party mattress 68 cannot interfere with the functioning of any of the other modules 24 that are on the Ethernet 26 other than footboard module 24b. In some embodiments of person support apparatus 20, one or more displays 38 are positioned at locations other than, or in addition to, the footboard 52. In those embodiments, VLAN 74a is configured to isolate the mattress module 24h and any one or more modules 24 that control the displays on which mattress data is to be displayed from the other modules 24. In other words, VLAN 74a can include other modules 24, either besides or in addition to, mattress module 24h.

A second VLAN 74b is included in the embodiment of person support apparatus 20 shown in FIG. 3. VLAN 74b isolates external device module 24i from all of the modules 24 of person support apparatus 20 (including mattress module 24h), except for footboard module 24b. VLAN 74b provides the same advantages of isolating third party external devices 66 from Ethernet 26 as VLAN 74a does for mattress module 24h. That is, VLAN 74b isolates from device 66 all of those modules 24 of Ethernet 26 except for footboard module 24b, which controls user interface 50 and its displays 38. VLAN 74b therefore limits the communication abilities of external device module 24i to only being able to communicate with footboard module 24b.

As shown in the embodiment of person support apparatus 20 of FIG. 3, Ethernet switch 28 includes seven ports. It will be understood that switch 28 can be replaced with another Ethernet switch having fewer or greater numbers of ports 62. Indeed, in some embodiments of person support apparatus 20, multiple Ethernet switches 28 are included on the same person support apparatus 20. Regardless of the number of ports and/or the number of switches 28, Ethernet switch 28 includes a MAC address associated with each port. In at least one embodiment, person support apparatus 20 is designed such that each of the modules 24 are assigned to, and coupled to, a pre-designated one of the ports 62 of switch 28. In this manner, when switch 28 is powered on and receives messages (e.g. Ethernet frames) from a particular port 62, it will know from what type of module 24 those messages are coming from (assuming the modules 24 are plugged into their correct ports 62 on switch 28). Thus, for example, if a particular port is assigned to be used for a propulsion control module 24g, then switch 28 will be able to recognize messages that come into that particular port 62 without having to receive and/or analyze any particular messages from propulsion control module 24g that identify itself as a propulsion control module 24g. In an alternative embodiment, any of the modules 24 can be plugged into any of the ports 62 of switch 28 and each of the modules 24 is configured to send a message to switch 28, and/or to a controller that oversees switch 28, that identifies what type of module it is.

In the embodiment of FIG. 3, Ethernet switch 28 is also in communication with a connectivity module 24f. Connectivity module 24f includes a microcontroller 30 and a WiFi (e.g. IEEE 802.11) radio 76. WiFi radio 76 is adapted to communicate with any other devices that are WiFi compatible and that are within range of WiFi radio 76, including, but not limited to, one or more wireless access points 132 (FIG. 5) of a healthcare facility's local area network 106. Connectivity module 24f converts messages received via the WiFi protocol into Ethernet frames that are then transmitted over Ethernet 26. Connectivity module 24f also converts messages received from Ethernet 26 that are to be transmitted off-board person support apparatus to the WiFi protocol. In the illustrated embodiment, person support apparatus 20 utilizes the Transmission Control Protocol/Internet Protocol (TCP/IP) suite of communication protocols for communicating at least some of its messages. The IP protocol includes IPv4 in some embodiments, IPv6 in other embodiments, and combinations of the two in still other embodiments.

Connectivity module 24f includes two Service Set Identifiers (SSIDs) 78a and 78b. A first SSID 78a is adapted to communicate with one or more wireless devices 82 that are manufactured by, or authorized by, the same manufacturer as the manufacturer of person support apparatus 20. This SSID 78a allows devices 82 that are connected to module 24f using SSID 78a to gain greater access to the resources of Ethernet 26 on person support apparatus 20 than are available using second SSID 78b. That is, devices 82 that couple to connectivity module 24f using first SSID 78a are authorized by connectivity module 24f to penetrate a firewall that is implemented by connectivity modules 24f.

In contrast, third party wireless devices 80 that couple to connectivity module 24f using the second SSID 78b are isolated by the firewall from communicating with many of the modules 24 of person support apparatus 20. For example, in one embodiment, second SSID 78b is provided to allow a third party wireless device 80 to utilize one or both of displays 38 in the same manner that external device module 24i has wired access to displays 38. That is, the built-in firewall of connectivity module 24f restricts the external third-party wireless devices 80 from communicating with selected ones of the modules 24 on person support apparatus 20. If second SSID 78b is intended to enable a wireless device 80 to utilize user interface 50 of person support apparatus 20, then the firewall of connectivity module 24f allows the wireless device 80 to communicate over Ethernet 26 with footboard module 24b, but not with any of the other modules 24.

In at least one embodiment, second SSID 78*b* enables one or more medical sensors and/or medical devices to communicate with person support apparatus 20 such that information gathered by the medical sensors and/or medical devices can be displayed on one or more of displays 38. For example, in one embodiment, second SSID 78*b* enables vital signs sensors (whether third party devices 80 or same party devices 82) that are worn by—or attached to—a patient positioned on person support apparatus to have their outputs displayed (and in some cases, recorded in a memory of footboard module 24*b*) on displays 38. This enables vital sign sensors or monitors that are too small for their own built-in display and/or user interface to be able to utilize the displays 38 and/or user interface 50 of person support apparatus 20 to display their outputs and/or control their operation.

In some embodiments, one or both of SSIDs 78*a* and *b* are not broadcast by connectivity module 24*f*, but instead are only available to devices that are otherwise aware of the existence of SSIDs 78*a* and/or 78*b*. This helps ensure greater security for accessing Ethernet 26. Still further, in some embodiments of person support apparatus 20, connectivity module 24*f* uses WiFi Protected Access (WPA) and/or WiFi Protected Access II (WPA2) with either or both of SSIDs 78*a* and 78*b* in order to further increase the security of the Ethernet 26 of person support apparatus 20.

Although FIG. 3 illustrates connectivity module 24*f* as communicating solely by WiFi, it will be understood that connectivity modules 24*f* can be modified so that the WiFi communication is replaced or augmented with other wireless communication types, including near field communication, such as disclosed in commonly assigned U.S. patent application Ser. No. 13/802,992 filed Mar. 14, 2013 by inventors Michael Joseph Hayes et al. and entitled COMMUNICATION SYSTEMS FOR PATIENT SUPPORT APPARATUSES, the complete disclosure of which is hereby incorporated by reference. Additionally or alternatively, still other types of communication protocols can be used with connectivity module 24*f*, such as the open access multicast wireless sensors network technology marketed by ANT Wireless, a division of Dynastream Innovations Inc. which has a principal place of business in Cochrane, Alberta, Canada. In such cases, wireless devices 80 that utilize the ANT network technology are able to communicate with connectivity module 24*f*, which can then display information from the devices 80 or, as will be discussed in greater detail below, forward the information gathered by the wireless device 80 to a healthcare facility network using communication resources of the person support apparatus 20. Devices 80 that utilize the ANT network technology often include multiple low-power sensors that are either attached to, or positioned in close proximity to, a patient supported on person support apparatus 20, or a caregiver associated with that patient. Still other types of communication protocols besides WiFi, near field, and ANT may be incorporated into connectivity module 24*f*.

Figure 4:
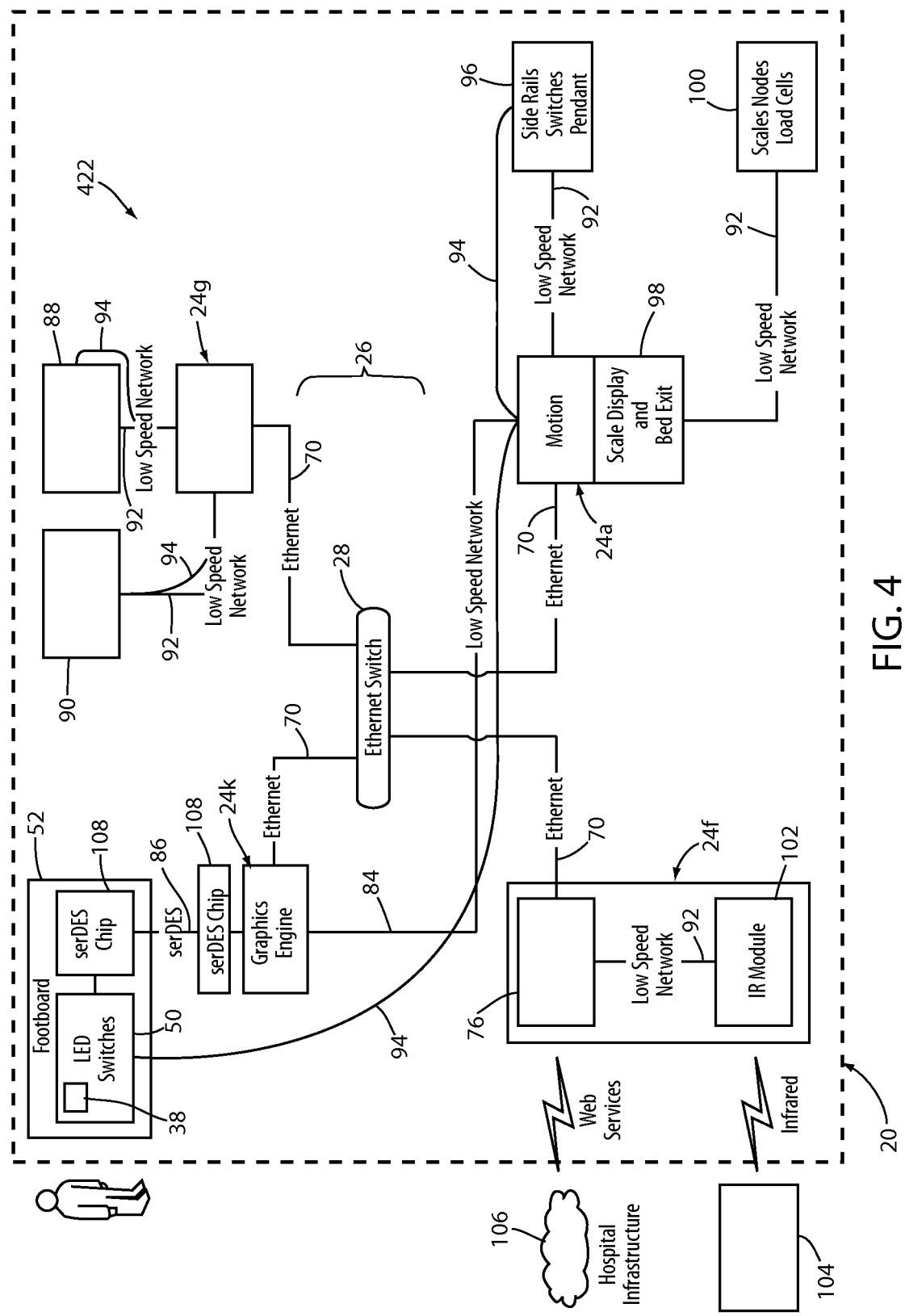
FIG. 4 is a block diagram of another embodiment of a communication system that is usable in the person support apparatuses and/or other devices described herein.

FIG. 4 illustrates another alternative embodiment of a communication system 422 that can be included in one or more of the person support apparatuses 20 and/or thermal control units 64 described herein. Those components of communication system 422 that are the same as communication system 22 and/or communication system 222 are labeled with the same reference numbers and operate in the same manner as previously described, unless explicitly stated otherwise. Those components of system 422 that are not found in systems 22 or 222 are provided with a new reference number and their construction and operation is described in more detail below.

Communication system 422 includes an Ethernet switch 28 that is communicatively coupled via a plurality of links 70 to a graphics engine module 24*k*, a motor control module 24*a*, and a propulsion control module 24*g*. Each of these links communicates with each other using Ethernet switch 28 and Ethernet links 70. Motor control module 24*a*, which is responsible for controlling the various motors on person support apparatus 20 (e.g. moving litter 42 up and down; pivoting the deck sections 48; etc.) also communicates with graphics engine module 24*k* over a lower speed network connection 84. Lower speed network connection 84 is, in some embodiments, a serial connection that uses one of the following communication protocols: an RS-232 protocol, an RS-422 protocol, an RS-485 protocol, an I-squared C protocol ($I^2C$), and an IEEE 1394 serial bus protocol (e.g. Firewire). Graphics engine module 24*k*, which controls the images displayed on a footboard display 38 mounted to footboard 52 of person support apparatus 20, also communicates with motor control module 24*a* over low speed network connection 84, in addition to Ethernet 26.

In one embodiment, motion commands that are received from a user at user interface 50 are transmitted to graphics engine module 24*k* over a serializer/deserializer (serDES) connection 86. Once received by graphics engine module 24*k*, graphics engine module 24*k* forwards the received motion commands to motor control module 24*a* over both Ethernet 26 and lower speed network 84. In response to the motion control commands, motor control module 24*a* starts or stops movement of one or more motors on person support apparatus. The duplicative forwarding of these motion control commands from graphic engine module 24*k* to motion control module 24*a* via both Ethernet 26 and network 84 is carried out primarily as a safety measure to ensure that movement of the components of person support apparatus 20 cannot be carried out solely on the basis of messages traveling on Ethernet 26. This helps reduce the possibility of inadvertent movement of person support apparatus 20, as well as resists the ability of an unauthorized individual and/or device from controlling movement of any of the movable components of person support apparatus 20.

In at least one embodiment, motion control module 24*a* is configured to carry out movement of one or more components of person support apparatus 20 if it receives a motion command from both Ethernet 26 and from lower speed network 84, or if it receives a motion command from only lower speed network 84 (and not Ethernet 26). In this embodiment, motion control module 24*a* will not move any components of person support apparatus 20 if it receives a motion control command only from Ethernet 26. Further, if motion control module 24*a* receives a motion control command from lower speed network 84, but not an accompanying motion control command from Ethernet 26, it will issue an error notification that indicates that there may be an error with Ethernet 26. It will, however, still carry out the movement associated with the motion control command it received via lower speed network 84. In an alternative embodiment, motion control module 24*a* is configured to only carry out movement of one or more components of person support apparatus 20 if it receives motion commands via both Ethernet 26 and lower speed network 84.

Other types of data, packets, and/or messages that are transmitted between motion control module 24*a* and graphic engine module 24*k* are not, in at least one embodiment, duplicatively communicated to each other over both Ethernet 26 and lower speed network 84. For example, in at least one embodiment, any sensor data, video data, voice-over-IP (VoIP) data, diagnostic data, and/or heartbeat messages that are transmitted between modules 24a and 24k are transmitted exclusively over Ethernet 26. In other embodiments, some or all of this data is transmitted duplicatively over both Ethernet 26 and network 84.

Propulsion module 24g is in communication with one or more handles 88 and/or buttons 90 that are used to control the automatic propulsion of person support apparatus 20 from one location to another. Propulsion module 24g communicates with handles 88 and buttons 90 via serial connections 92 that are separate from, and not in direct communication with, lower speed network 84. In some embodiment, some of serial connections 92 are implemented as low voltage differential signaling (LVDS) connections, although it will be understood that other types of serial connections can be used. A safety enable link 94 is also coupled between propulsion module 24g and each of handles 88 and buttons 90. A similar safety enable link 94 is also coupled between user interface 50 and motion control module 24a, as well as between one or more siderail user interfaces 96. The purpose and operation of these safety enable links 94 is described in more detail below with specific reference to FIG. 6.

Motion control module 24a includes, in the embodiment shown in FIG. 4, a scale and exit detection subsystem 98. Scale and exit detection subsystem 98 is in communication with a plurality of load cells 100 that are positioned generally adjacent each corner of litter 42 (when person support apparatus 20 is implemented as a bed, cot, or stretcher), and generally adjacent each corner of the seat (when person support apparatus 20 is implemented as a chair). The outputs from load cells 100 are monitored by motion control module 24a to not only detect the weight of a person supported on person support apparatus 20, but also to issue alerts when the person may be about to, or has already, exited person support apparatus 20. The load cells communicate with subsystem 98 via a serial link 92. In at least some embodiments, scale and exit subsystem 98 is constructed, and operates, in the same manner as disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, scale and exit subsystem 98 is configured in any of the manners disclosed in commonly assigned U.S. patent application Ser. No. 62/076,005 filed Nov. 6, 2014 by inventors Marko N. Kostic et al. and entitled EXIT DETECTION SYSTEM WITH COMPENSATION, or in commonly assigned U.S. patent application Ser. No. 62/065,242 filed Oct. 17, 2014 by inventors Marko N. Kostic et al. and entitled PATIENT SUPPORT APPARATUSES WITH MOTION MONITORING, the complete disclosures of both of which are hereby incorporated herein by reference. Still other types of scale and exit detection subsystems may alternatively be used.

In the embodiment of connectivity module 24f shown in FIG. 4, connectivity module 24f includes, in addition to a WiFi radio 76, an infrared module 102 that is adapted to communicate with a stationary location transceiver 104. Stationary location transceivers 104 are positioned around a healthcare facility at known locations and have a limited communication range (e.g. about 6 feet, although other ranges are possible). Further, each stationary location transceiver 104 has a unique ID. When installed in a healthcare facility, the locations of each of the transceivers 104 are mapped so that a data table correlating the unique ID of each transceiver with the location of that particular transceiver in the healthcare facility is created. This table is used to determine the location of person support apparatuses 20. That is, when a person support apparatus 20 is able to communicate with a particular transceiver 104, the person support apparatus must be in close proximity to the particular transceiver. Accordingly, the person support apparatus 20 is determined to be at the location of the particular transceiver 104 that it is able to communicate with.

In one embodiment, transceiver 104 transmits its unique ID to person support apparatus 20, which receives it via IR module 102. Person support apparatus 20 then forwards this unique ID, along with an ID number corresponding to the unique identity of that person support apparatus, to a healthcare network, such as healthcare facility network 106 (FIG. 4). A server on the healthcare facility network 106 contains the data table that correlates all of the transceiver 104 IDs to their respective locations within the healthcare facility. By utilizing this table, the server looks up the particular transceiver ID in the table and determines that the particular person support apparatus 20 (the one whose ID was transmitted with the transceiver 104 ID) that transmitted the transceiver ID is at the same location as the transceiver 104. In another embodiment, the data table containing the locations of all of the transceivers 104 and their respective locations within the healthcare facility is downloaded to each person support apparatus 20 and stored in its internal memory. One of the modules 24 on person support apparatus 20 then utilizes this table to determine the location of person support apparatus 20 within the healthcare facility. This location is then used in some communications between person support apparatus 20 and servers or other devices on the healthcare network 106. In still other embodiments, IR module 102 and stationary transceiver 104 can be modified to function in any of the manners disclosed in commonly assigned U.S. Pat. No. 8,674,826 issued to Becker et al. and entitled LOCATION DETECTION SYSTEM FOR A DEVICE, the complete disclosure of which is hereby incorporated herein by reference.

In the embodiment of person support apparatus 20 shown in FIG. 4, graphics engine module 24k is physically positioned on litter 42, and not on or in footboard 52. A serDES connection 86 runs from the graphics engine module 24k to the footboard 52. The serDES connection allows the graphic images that are output from the graphics engine to be converted to a serial format that is then sent over the serDES connection to footboard 52 for display on display 38. In other words, graphics engine module 24k, among other responsibilities, controls the images that are displayed on display 38 of person support apparatus 20. By utilizing this serDES connection, a simplified electrical connector can be used on both the litter and on the footboard that electrically bridges the two when the footboard 52 is mounted on the person support apparatus 20 (footboard 52 is removable from person support apparatus 20). That is, it is not necessary to include a large number of electrical pins that must align with a corresponding receptacle in order to bridge the electrical connection between the footboard and the person support apparatus, such as is required when sending data in a parallel fashion or otherwise using multiple connections.

In addition to simplifying the electrical connector between the footboard and person support apparatus 20, the use of serDES connection 86 also enables footboard 52 to include one or more displays 38 without also including a microcontroller within footboard 52. Instead, footboard 52 includes a conventional, off-the-shelf serDES chip 108 that deserializes the incoming data from graphics engine module 24k and distributes the data among the electrical components of footboard 52, as well as serializes the outgoing data from footboard 52 that is sent to graphics engine module 24k. Similarly, graphics engine module 24k includes a conventional, off-the-shelf serDES chip 108 that deserializes the incoming data from footboard 52 and serializes the outgoing data that is sent to footboard 52. By utilizing these serDES chips 108, which are less expensive than microcontrollers, the cost of replacing missing or damaged footboards 52 become less expensive.

In at least one embodiment, graphics engine module 24k transmits to footboard 52 over serDES connection 86 images that are to be displayed on display 38 that were formatted in a scalable vector graphics (SVG) format. This enables a first footboard 52 to be replaced with a second footboard 52 having another display 38 on it that is of a size different from the size of the display of the first footboard 52 without requiring any reprogramming on the part of graphics engine module 24k. In other words, graphics engine module 24k contains memory that stores the images to be displayed on display 38 in an SVG format. Prior to transmitting these images to display 38, graphics engine module 24k scales these SVG formatted images to a size that matches the size of the display 38 that is included on footboard 52. Because the images are stored and/or created in an SVG format, graphics engine module 24k can easily re-size the images prior to transmission to footboard 52 without loss of fidelity of the graphic images, and without having to be reprogrammed to generate images that are specifically sized and/or formatted to the particular display that is included with footboard 52. In order to resize the SVG images to the appropriate size, footboard 52 transmits to graphics engine module 24k a message that identifies the size of display 38 to graphics engine module 24k so that graphics engine module 24k knows what size to scale the SVG image to. After this message is received, graphics engine module 24k re-sizes the image data appropriately prior to transmitting it to footboard 52 over serDES connection 86.

The use of SVG graphics for displaying images on display 38 enables different footboards 52 having different sized displays 38 to be swapped with each other for use on person support apparatus 20 without requiring any changes or reprogramming of graphics engine module 24k, or any other components of person support apparatus 20. Further, because graphics engine module 24k is physically located on litter 42, rather than incorporated into footboard 52, upgrading of footboards 52 having a smaller sized display 38 to footboards 52 having a larger sized display 38 can be accomplished in a more cost-effective manner.

Figure 5:
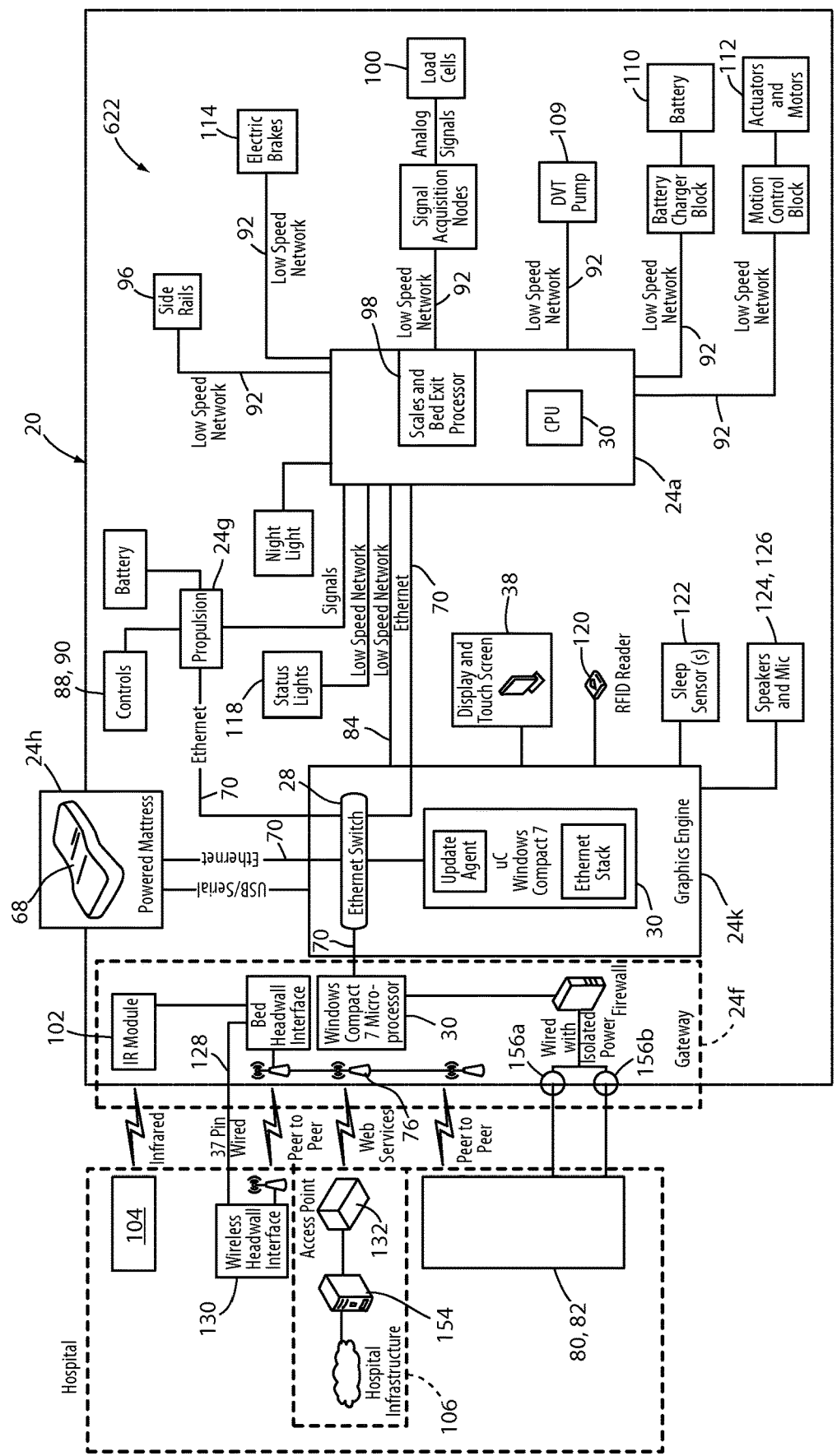
FIG. 5 is a block diagram of still another embodiment of a communication system that is usable in the person support apparatuses and/or other devices described herein.

FIG. 5 illustrates another alternative embodiment of a communication system 622 that can be included in one or more of the person support apparatuses 20 and/or thermal control units 64 described herein. Those components of communication system 622 that are the same as those found in any of communication systems 22, 222, and/or 422 are labeled with the same reference numbers and operate in the same manner as previously described, unless explicitly stated otherwise. Those components of system 622 that are not found in systems 22, 222, or 422 are provided with a new reference number and their construction and operation is described in more detail below.

Communication system 622 includes an Ethernet switch 28 that is communicatively coupled via a plurality of links 70 to a graphics engine module 24k, a motor control module 24a, a propulsion control module 24g, a mattress control module 24h, and a connectivity module 24f. Each of these links communicates with each other using Ethernet switch 28 and Ethernet links 70. As in system 422, motor control module 24a and graphics engine module 24k also communicate with each other over a lower speed network connection 84. Lower speed network connection 84 is, in some embodiments, a serial connection that uses one of the following communication protocols: an RS-232 protocol, an RS-422 protocol, an RS-485 protocol, an I-squared C protocol ($I^2C$), and an IEEE 1394 serial bus protocol (e.g. Firewire). Further, as with communication system 422, motor control module 24a and graphics engine module 24k utilize Ethernet 26 and network connection 84 in the same manner as was described above with respect communication system 422. That is, motion control commands that are sent to motor control module 24a are only acted upon if they are received on at least lower speed network connection 84, and are not acted upon if they are only received via Ethernet 26.

Motor control module 24a of communication system 622 includes, in addition to those components previously described, a plurality of serial connections 92 to a Deep Vein Thrombosis (DVT) pump 109, a battery 110, one or more actuators or motors 112, an electric brake 114, a night light 116, and one or more status lights 118. Motor control module 24a controls and/or receives data from all of these devices. In some cases, the data received from one or more of these devices is transmitted over Ethernet link 70 to graphics engine 24k where some or all of it is displayed on display 38. In some cases, the data received from one or more of these devices is also transmitted over Ethernet link 70 and through switch 28 to connectivity module 24f where some or all of the data is forwarded off-board person support apparatus 20 to one or more devices or structures (e.g. healthcare network 106, third party device 80, same party device 82, etc.).

Graphics engine module 24k of communication system 622 includes, in addition to those components previously described, a plurality of serial connections 92 to an RF ID reader 120, a sleep sensors 122, one or more speakers 124 and microphones 126. RF ID reader 120, in one embodiment, is adapted to wirelessly detect RF ID tags that are worn by caregivers, patients, visitors, technicians, janitorial staff, and/or other types of individuals who may come into the vicinity of person support apparatus 20. RF ID reader 120 detects the presence of these RF ID tags, determines either the specific individual associated with the RF ID tag or the type of person associated with the RF ID tag (e.g. doctor, nurse, visitor, volunteer, etc.), and takes one or more actions in response to this determination.

In at least one embodiment, graphics engine module 24k changes the data that is displayed on display 38 in response to detecting the presence of an RF ID-tagged individual. More specifically, in at least one embodiment, module 24k changes the information displayed on display 38 to more closely align with the type of individual whose presence was detected. That is, for example, if a technician's presence is detected, control module 24k changes to displaying diagnostic information, service histories, model numbers, software updates, and other information that would likely be useful to the technician. If a nurse or doctor's presence is detected, graphics engine module 24k changes display 38 so that it displays information that is relevant to the care of the patient who is associated with person support apparatus 20, such as, but not limited to, the patient's weight and weight history, any vital signs that are being detected, the patient's name, the status and/or history of any therapy that has been—or is being—performed on the patient, and other data.

When changing the data that is displayed on display 38 in response to the presence of an RF-ID tagged individual within the vicinity of person support apparatus 20, graphics engine module 24k does not prevent—in at least some embodiments—the individual from accessing other information stored on person support apparatus 20 and eventually displaying it on display 38. That is, graphics engine module 24k does not lock out access to other information in response to an RF-ID tagged individual, in at least some embodiments, but still allows the individual to utilize user interface 50 to change the menus, pages, and/or other windows that are displayable on display 38 so that other information can be displayed. Graphics engine module 24k therefore merely gathers the information that is deemed most likely relevant to the RF ID-tagged individual and automatically displays that initially, while still allowing the individual to change the information that is displayed upon proper manipulation of user interface 50. In still other embodiments, graphics engine module 24k locks out access to certain pieces of information, depending upon the specific individual, or specific type of individual, whose RF ID tag has been sensed.

Sleep sensor 122 is adapted to detect, either alone or in combination with information from one or more sensors (such as, but not limited to load cells 100), whether a person supported on person support apparatus 20 is currently awake or asleep. In at least one embodiment, sleep sensor 122 is constructed in any of the manners disclosed in commonly assigned PCT publication WO 2014/151577 filed Mar. 13, 2014 by applicant Stryker Corporation and entitled PATIENT SUPPORT APPARATUS WITH PATIENT INFORMATION SENSORS, the complete disclosure of which is hereby incorporated herein by reference. The determination that a person supported on person support apparatus 20 is currently sleeping is forwarded by graphic engine module 24k to connectivity module 24f, in at least one embodiment, where this determination is then forwarded to one or more off-board devices in order to silence or reduce the volume of aural indicators, or otherwise alter the environment of person support apparatus 20 in a manner that is more conducive to the continued slumber of the person. Several of such actions are described in greater detail in the aforementioned WO 2014/151577 patent application.

Microphone 126 and speaker 124 are provided for enabling a person positioned on person support apparatus 20 to aurally communicate with one or more remotely located individuals, such as one or more remotely positioned nurses. In one embodiment, analog voice signals that are detected by microphone 126 are digitized, packetized, and sent over Ethernet link 70 to connectivity module 24, which then transmits the digitized voice packets to a remotely positioned nurse call station. The transmission of these voice packets may take place via WiFi radio 76 that is in communication with a wireless access point 132 of healthcare network 106, or via a nurse call cable 128 that is coupled between person support apparatus 20 and a nurse call system interface 130 mounted in the headwall of the hospital room. In some embodiments, the voice packets are transmitted from connectivity module 24f to the nurse call system interface via a wireless connection, such as is disclosed in commonly assigned U.S. patent application Ser. No. 62/035,656 filed on Aug. 11, 2014 by inventors Krishna Bhimavarapu et al. and entitled PATIENT SUPPORT APPARATUSES WITH WIRELESS HEADWALL COMMUNICATION, the complete disclosure of which is hereby incorporated herein by reference. The nurse's voice signals that are received at connectivity module 24f (whether from WiFi radio 76, nurse call cable 128, or by other means) are then packetized—if not packetized already—and transmitted over Ethernet link 70 to graphic engine module 24k, which then forwards them to speaker 124 for playback.

In some embodiments, the transmission of audio packets over Ethernet 26 utilizes the UDP protocol (User Datagram Protocol) of the Internet Protocol (IP) suite. Such UDP packets are encapsulated inside of Ethernet frames. In another embodiment, the transmission of audio packets over Ethernet 26 is carried out using conventional Voice over IP (VoIP) methods. In still other embodiments, audio packets are transmitted over Ethernet 26 using the $I^2S$ (aka Inter-IC Sound, or Integrated Interchip Sound, or IIS) standard developed by Philips Electronics of the Netherlands. In some embodiments, the $I^2S$ protocol is used for communicating audio over one or more of the lower speed network connections 84.

Connectivity module 24f, in the embodiment shown in FIG. 5, also includes in addition to WiFi radio 76, a Bluetooth (e.g. IEEE 802.15.1) transceiver 134 and a ZigBee (e.g. IEEE 802.15.4) transceiver 136 that are in communication with processor 30 of connectivity module 24f. In one embodiment of person support apparatus 20, connectivity module 24f uses Bluetooth transceiver 134 to wirelessly communicate with nurse call system interface 130. In other embodiments, Bluetooth transceiver 134 it used to communicate with one or more third party and/or same party external devices 80, 82, as was described previously. ZigBee transceiver 134 is utilized, in at least one embodiment, to wirelessly communicate with one or more of the external devices 80, 82.

Connectivity module 24f also includes first and second wired ports 156a and 156b (FIG. 5). At least one of ports 156a and 156b, in one embodiment, is an RJ-45 port that is positioned at a convenient location for enabling one or more external devices 80, 82 to couple connectivity module 24f, which in turn is coupled to Ethernet 26. In some embodiments of person support apparatus 20, microcontroller 30 oversees a $1^{st}$ application programming interface (API) associated with one or both of ports 156a or 156b that enables a device coupled to ports 156a or 156b (e.g. 80 or 82) to communicate data for display on display 38 and/or to receive data from user interface 50 for controlling one or more features of the external device. In some embodiments of person support apparatus 20, microcontroller 30 alternatively or additionally oversees a $2^{nd}$ API associated with ports 156a and/or 156b that enables a device coupled to ports 156a, 156b to communicate data for transmission by connectivity module 24f to healthcare network 106 utilizing the WiFi radio 76 of person support apparatus 20. By publishing these APIs, third party manufacturers of medical devices that do not have their own displays 38, user interfaces, and/or WiFi radios can configure their devices to be coupled to person support apparatus 20 in order to utilize the display 38, user interface 50, and/or WiFi radio 76 of person support apparatus 20.

Figure 6:
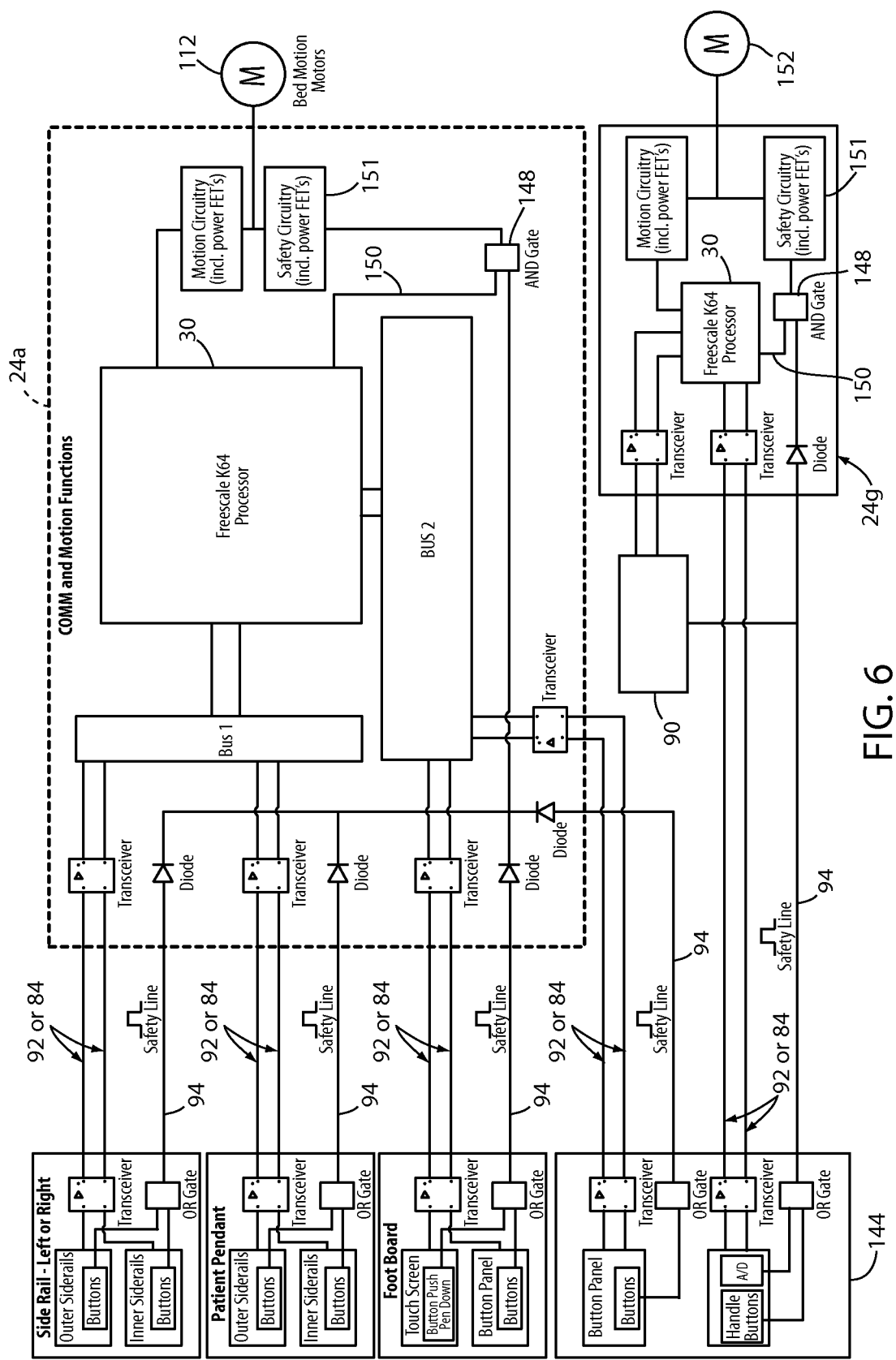
FIG. 6 is a diagram of a safety enable subsystem of the communication systems of FIGS. 4 and 5.

FIG. 6 illustrates in greater detail one manner in which the safety enable links 94 utilized in systems 422 and 622 can be implemented. Safety enable links 94 run between motion control module 24a and a siderail control panel 138 (or more than one siderail control panels 138), a patient control pendant 140, a footboard control panel 142 (which may be the same or different from user interface 50), and a propulsion control panel 144. Safety enable links 94 are utilized any time a person presses on a button, or otherwise manipulates an input, that controls movement of any component of person support apparatus 20. Whenever such a button or input is pressed or activated, a high voltage is fed to an OR gate 146 positioned within the control unit (e.g. panels 138, 142, 144, and/or pendant 140). The OR gate 146 connects together the various buttons or other inputs such that, if anyone of them is pressed, a voltage is fed to the corresponding safety enable line 94. The safety enable lines 94 are all fed to an AND gate 148 that is logically ANDed with an enable output 150 from processor 30 of motion control module 24a. The output of the AND gate 148 is fed to a safety circuit 151 that only allows the corresponding motor/actuator 112 to operate if both the output 150 and the safety enable line have high voltages. The processor 30 from motion control module 24a only creates a high voltage at output 150 if it receives a motion command from one of the control units (e.g. panels 138, 142, 144, and/or pendant 140) via one of the low speed network connections 84 or 92. Therefore, the motor/actuators 112 are never operated unless both the processor 30 of motion control module 24 receives a motion control command via a low speed connection 84, 92 and AND gate 148 receives confirmation via safety enable link 94 that a motion control button or input has been activated. This ensures that motors/actuators 112 are never operated based solely upon messages transmitted over low speed networks 84 or 92. Safety enable links 94 are physically separate from low speed network connections 84, 92, and safety enable links 94 couple directly from the button or input to motion control module 24a without passing through any intermediate control modules 24.

At least one safety enable link 94 also connects between propulsion control panel 144 and propulsion control module 24g. This safety enable link 94 operates in the same manner as described above and ensures that a propulsion motor 152 cannot be operated based solely upon serial messages that are received at processor 30 of propulsion control module 24g.

In some embodiments of any one or more of the communication systems 22, 222, 422, and/or 622 disclosed herein, Ethernet switch 28 and/or a processor 30 coupled to Ethernet switch 28 are configured to assign each control module 24 a fixed IP address. Thus, for example, control module 24a is assigned a first fixed IP address, control module 24b is assigned a second fixed IP address, and so on. In this manner, the other modules will know that any messages that identify the sender using the first IP address were transmitted by motion control module 24a, any messages that identify the sender using the second IP address were transmitted by footboard module 24b, and so on.

In alternative embodiments, any one or more of the communication systems 22, 222, 422, and/or 622 have an Ethernet switch 28 and/or a processor 30 coupled to the Ethernet switch 28 that include a Dynamic Host Configuration Protocol (DHCP) server. The DHCP server, which is internal to person support apparatus 20, leases IP addresses to the various modules 24 that are connected to Ethernet 26, as well to any one or more of the external devices 80, 82 that may be coupled to Ethernet 26. In one embodiment, the DHCP server issues leases of different lengths based upon whether or not the requesting lessee is a third party device/module or a device/module that was manufactured or approved of by the same entity that manufactured person support apparatus 20. For example, in one embodiment, the DHCP server issues longer leases to modules 24a-g and same-party devices 82 than it does to third party device 80. The length of the IP leases that are granted to mattress module 24h and external device module 24i varies depending upon the manufacture of the modules 24h or 24i is the same or different than the manufacturer of person support apparatus 20. When IP addresses are leased with shorter lease lengths to third party devices, in at least one embodiment, the third-party leases are on the order of one minute. Such short lease lengths help prevent unauthorized access to the components of person support apparatus 20 via third party devices.

In any of the communication systems 22, 222, 422, and/or 622 disclosed herein, Ethernet 26 is additionally utilized to transfer software updates to the various microcontrollers 30 of modules 24, or any other microcontrollers that are coupled to one or more of the modules 24. That is, software updates that are received by the person support apparatus 20 are transmitted over one or more Ethernet links to the module 24 and/or microcontroller whose software and/or firmware is intended to be updated. Such software updates may be carried out in at least four different manners.

In a first manner, each of the modules 24 includes a Universal Serial Bus (USB) port into which a thumb drive, or other USB-compatible device, may be inserted that contains the updated software that is to be conveyed to person support apparatus 20. A service technician, or other authorized individual, plugs in the USB-compatible device, which may be a laptop or other computer with a USB cable in at least some embodiments, and the new software is downloaded to the module 24. The microcontroller receives a command from the external USB compatible device to enter its boot loader mode, and the new software is thereafter installed in the corresponding memory of the updated microcontroller.

In a second manner, at least one, but not all, of the modules 24 includes a Universal Serial Bus (USB) port into which a thumb drive, or other USB-compatible device, may be inserted that contains the updated software that is to be conveyed to person support apparatus 20. A service technician, or other authorized individual, plugs in the USB-compatible device, which may be a laptop or other computer with a USB cable in at least some embodiments, and the new software is downloaded to the module 24 having the USB port. If the updated software is to update a different module 24 than the one with the USB port, the receiving module 24 forwards the updated software to the intended module 24 over Ethernet 26. The microcontroller that is the intended recipient also receives a command from the external USB compatible device (e.g. thumb drive, computer, etc.) to enter its boot loader mode, and the new software is thereafter installed in the corresponding memory of the updated microcontroller.

When implementing this second manner of updating the software for one or more modules 24, the graphics engine module 24k oversees the transfer and installation of new software to the other nodes 24. Graphics engine module 24k first examines the packets of the new software update to determine which module 24 is the intended recipient. If the intended recipient is the graphics engine module 24k itself, it sends out a message to the other modules 24 indicating that it will be unavailable while its software is being updated. It therefore will not issue a heartbeat message, or respond to a heartbeat message that is issued by another module (as discussed in more detail below) during the software updating process. Graphics engine module 24k will then finish up any other tasks that need to be performed prior to updating its own software. If the intended recipient is not graphics engine module 24k itself, graphics engine module 24k sends a message to the intended recipient informing it that it has a software update for it. Instead of forcing the software update onto the recipient module, graphics engine module 24k waits for a reply back from the recipient module 24 that indicates that it is ready for installing the new software. In this manner, the intended recipient module 24 is able to complete current tasks it is performing. The intended recipient thereafter switches into boot loader mode and graphics engine module 24k transfers the updated software to the recipient module's microcontroller 30 over Ethernet 26. If the microcontroller is located somewhere on person support apparatus 20 that is not in communication with Ethernet 26, graphics engine module 24k transfer the updated software to the microcontroller over lower speed network 84.

In a third manner, software is updated on one or more of modules 24 by receiving the software from a cloud based server (not shown) and/or from a server 154 (FIG. 5) coupled to the healthcare facility network 106. If the software originally resides on a cloud-based server, the updated software is first transferred from the cloud-based server to the local server 154 through the healthcare network 106's Internet gateway or Internet server. In some instances, healthcare facility network 106 will include a firewall and/or other security measures that may hinder or prevent the cloud-based provisioning of the software update. In those instances, the updating of software on person support apparatus 20 may utilize software that the healthcare facility already it using that allows access through the security features of the healthcare network 106. That is, commercially available tunneling software may be used that enables the software update to be transferred from the cloud to server 154 of healthcare network 106 through the healthcare facility's firewall or other security features. Such commercial software is available from multiple vendors. In one embodiment, software from Axeda Corporation of Rochester, N.Y., is used, including one or more cloud servers of Axeda Corporation that are authorized for communication with healthcare network 106. When using software and cloud servers from Axeda Corporation, the entity providing the updated software first transfers the updated software to the Axeda servers where it is thereafter forwarded to healthcare network 106. Other software may also be used.

Once the software update is present on local server 154, it is forwarded to connectivity module 24f of person support apparatus 20 using one of the various transceivers contained within connectivity module 24f, such as, but not limited to, WiFi radio 76. In one embodiment, connectivity module 24f forwards the updated software to graphic engine module 24k over Ethernet 26, and graphics engine module 24k then determines the intended recipient of the software and distributes it to the intended recipient. In another embodiment, connectivity module 24f itself determines the intended recipient of the updated software and distributes it to the intended recipient using Ethernet 26 and/or lower speed network 84.

In a fourth manner, software updates to person support apparatus 20 are provided by a technician who creates a local virtual or temporary network in the vicinity of person support apparatus 20 and transmits the updated software over the virtual or temporary network. In one embodiment, the technician brings a laptop having a WiFi transceiver and the laptop includes software that broadcasts a specific SSID that the person support apparatus 20 is programmed to connect to using WiFi radio 76. Once connected, the updated software is transmitted via WiFi to connectivity module 24f and distributed in any of the manners discussed above. In some embodiments, the person support apparatus 20 is preprogrammed to respond and couple to a specific SSID anytime the WiFi radio detects this SSID. In another embodiment, an instruction is given to the person support apparatus 20 to connect to the specific SSID the next time the person support apparatus 20 boots up, or at some other predetermined time. Once the updated software has been transmitted to person support apparatus 20, WiFi radio 76 is programmed to disconnect from the specific SSID used to download the software updates and reconnect to the SSID of the healthcare network 106.

Person support apparatus 20, in at least one embodiment, is configured to display one or more instructional videos on display 38 that provide instructions and/or other guidance about how to use one or more features of person support apparatus 20, or one or more features of any of the external devices 80, 82, and/or one of more features of mattress 68. In some embodiments, these video files are stored at locations on person support apparatus 20 other than footboard module 24b, which controls display 38. In those instances, the video files are transmitted over Ethernet 26 footboard module 24b, which then displays them on display 38. Updates and/or additions to such instructional videos can be accomplished in the same manner as any of the different manners discussed above for updating software on person support apparatus 20.

In some embodiments, the video files for the instructional videos are stored off-board person support apparatus 20, such as in the internal memory of any of devices 80, 82, and/or mattress 68. The video files are then transmitted to person support apparatus 20 over the connection between these devices and person support apparatus 20, which receives the video files and forwards them over Ethernet 26 to footboard module 24b.

In one embodiment of communication systems 22, 222, 422, and 622, each module 24 that is coupled to Ethernet 26 includes conventional status Light Emitted Diodes (LEDs) that provide an indication of the rate at which data is being transmitted over the Ethernet link 70 as well as an indication of network activity. In another embodiment of communication systems 22, 222, 422, and 622, status LEDs are provided at a centralized location for all of the Ethernet links 70, such as at graphics engine module 24k. By providing such status LEDs at a unified location, a technician is able to monitor the health and/or activity of the entire Ethernet 26 from a single location. In still another embodiment of communication systems 22, 22, 422, and 622, status LEDs are provided on each module 24 as well as at a unified location on a selected one of modules 24.

In at least one embodiment, the individual pixels that define one or more images that are to be displayed on display 38 are transferred to footboard module 24b over Ethernet 26, rather than being generated locally by footboard module 24b or retrieved from one or more memories local to footboard module 24b. This enables a new module 24 that is added to person support apparatus 20, or an existing module 24 that is upgraded, to generate new images on display 38 without having to change any of the software of footboard module 24b, or otherwise upgrade software module 24b. Thus, for example, if a propulsion control system is added to person support apparatus 20 (including propulsion control module 24g), propulsion control module 24g can transmit images to footboard module 24b that are to be displayed on display 38 that correspond to that particular propulsion system. Similarly, if a new mattress module 24h is added to person support apparatus 20, the new mattress module 24h can transmit images to footboard module 24b that are to be displayed on display 38 that correspond to that particular mattress. Footboard module 24b can therefore accommodate new graphics for new modules 24b without having to be reprogrammed with the new graphics and/or without having to be originally programmed with the graphics for the new modules 24. In at least one embodiment, one or more modules 24 transmit to footboard module 24b real time images that provide feedback to a viewer about an ongoing process onboard person support apparatus 20, or onboard a device communicatively coupled to person support apparatus 20 (e.g. 80, 82, 68). The real time images are transmitted via Ethernet 26. The real time images specify the pixels that are to be displayed on display 38, rather than merely specifying data that is to be displayed on display 38 via pixels that are selected and defined by footboard module 24b.

In some embodiments, the images that transmitted to footboard module 24b for display on display 38 are displayed by footboard module 24b over the entire display 38. In other embodiments, the images received by footboard module 24b are displayed over only a portion of display 38. In still other embodiments, footboard module 24b displays one or more menus that allow a user to selectively view the images received by footboard module 24b on display 38. In still other embodiments, display 38 is a touchscreen and pressing on the appropriate location of the touchscreen causes a toggling between displaying the images on display 38 and displaying other images on display 38. In still other embodiments, multiple of these manners of displaying the images are combined.

In any one or more of communication system embodiments 22, 222, 422, and/or 622, Ethernet switch 28 is configured to implement a prioritization scheme for packets traveling over Ethernet 26. For example, in one embodiment, Ethernet switch 28 is configured to filter out any packets having IP addresses (either in the destination or the source fields) that do not correspond to motion control module 24a during certain specified periods of time. This guarantees that motion control communication will always be guaranteed time for communication over Ethernet 26. Switch 28 then divides up the remaining time periods between the other modules 24 coupled to Ethernet 26 and allows them time to communicate. Depending upon the traffic conditions on Ethernet 26, Ethernet switch 28 is configured, in at least one embodiment, to stop allowing any additional modules or nodes 24 to be added to Ethernet 26 if excessive traffic is present, or there are currently as many nodes present on Ethernet 26 that switch 28 is capable of assigning communication time slots to. In other words, switch 28 may stop allowing additional nodes 24 to join Ethernet 26 if there is a risk of starving one or more nodes of communication time slots.

In still other embodiments, Ethernet 26, or components of Ethernet 26, are implemented as EtherCAT (Ethernet for Control Automation Technology), which has been standardized in IEC 61158. T In any one or more of communication system embodiments 22, 222, 422, and/or 622, one or more of the links 70 of Ethernet 26 are configured to transfer power as well as data (e.g. Power over Ethernet, or PoE). In some embodiments, such PoE links 70 are used to wake up one or more modules 24 that enter a sleep mode in which they draw significantly less, or zero, power as compared to when they are not in sleep mode. The power that is transmitted over the PoE link 70 is used to power the circuitry that wakes up the module 24 receiving the wake up command. Once woken up, the module 24 resumes drawing power from its main source, or in some cases, continues to be powered by the power supplied by the PoE link 70.

In some embodiments of person support apparatus 20, one or more of the modules 24 includes a web server that is executed by microcontroller 30, or by some other microcontroller or microprocessor contained within each module 24. The web server servers up web pages for the module 24 that provides past and current status and diagnostic information. When a technician couples his or her computer that is running a web browser to Ethernet 26, in any of the ways discussed above (e.g. plugging an Ethernet cable into port 156a and/or coupling wirelessly to Ethernet 26 via WiFi radio 76), the technician is able to browse to the web page of each of these web servers to view the contents of the diagnostic and status information. In at least one embodiment, all of the web servers for a particular module 24 are the same for each person support apparatus 20. In that manner, the technician's web browsing software can be preprogrammed with the IP addresses necessary to view the web page of each module 24. The web servers update the diagnostic and status information in real time, as well as maintaining a log of significant events—all of which are viewable and/or downloadable from the web servers of modules 24. Still further, in at least one embodiment, a technician can access these web servers remotely, such as by connecting from a remote location to healthcare network 106, or by connecting to healthcare network 106 in a different location than the location of person support apparatus 20. In addition to the status and/or diagnostic information, the web servers are programmed, in at least one embodiment, to identify the software and/or firmware version of their corresponding module, as well as to provide maintenance logs of any past maintenance work that was done regarding components associated with that particular module.

In some embodiments of person support apparatus 20, one of the modules 24 sends out a periodic heartbeat message to the other modules. The heartbeat message informs the other modules of the continued presence and proper operation of the module that is transmitting the heartbeat message. In still other embodiments, each of the modules 24 is programmed to respond to the heartbeat message with an acknowledgement. In this manner, the module 24 that sends out the heartbeat message is able to maintain knowledge of which modules 24 are currently present on Ethernet 26.

Although communication systems 22, 222, 422, and 622 have been described herein primarily as consisting of a single Ethernet 26, it will be understood by those skilled in the art that person support apparatus 20 can be modified to include multiple Ethernets 26. For example, in some embodiments, a second Ethernet 26 is provided the carries specific types of communications between user interface 50 (including display 38) and connectivity module 24f. In one embodiment, those specific types of communications include any communications that originate from an off-board source, or that are to be transmitted to an off-board source. By including a second Ethernet 26 for such off-board communication, access to the first Ethernet 26, which is used to control the internal operations of person support apparatus 20, cannot be gained. This helps prevent unauthorized persons, entities, and/or devices from gaining access to the internal workings of person support apparatus 20 using any of the ports, radios, or other transceivers on-board.

In at least one embodiment of each of the communication system 22, 222, 422, and 622 described above, each module 24 that is coupled to Ethernet 26 is coupled thereto using one or more media independent interfaces that enable the module 24 to be communicatively coupled to different physical media or links 70 (e.g. twisted pair copper, fiber optic, etc.).

In at least one embodiment of each of communication systems 22, 222, 422, and 622 described above, connectivity module 24f performs network address translation when the TCP/IP packets that are transmitted internally on Ethernet 26 are transmitted off-board the person support apparatus 20 to an external device (e.g. 80, 82), and/or when TCP/IP packets are received by connectivity module 24*f* from any such external device and transmitted over Ethernet 26. In those embodiments of person support apparatus 20 that include web servers associated with one or more modules 24, the web browser that accesses these web servers sends a message that is addressed to the IP address of the connectivity module 24*f*, but contains within its payload the IP address of the specific module 24 whose web server it is attempting to access. Connectivity module 24*f* receives the off-board message that was sent to its IP address and forwards it to the on-board correct module 24 using the IP address of that on-board module 24. Conversely, for outgoing traffic, connectivity module 24*f* receives messages from the on-board module 24 that are addressed to its IP address, which it then re-packages to include the IP address of the device hosting the web browser before sending those re-packaged messages off of person support apparatus 20.

In at least one embodiment of each of communication systems 22, 222, 422, and 622 described above, motion control module 24*a* is configured to transmit motion count sequences over Ethernet 26 to another module 24 that allows for processing of the motion count sequences to be performed at a module 24 other than motion control module 24*a*. That is, although motion control module 24*a* is configured to control the motion of various components of person support apparatus, the position, speed, and/or other feedback signals from the actuators and/or motors is processed by another module 24, thereby off-loading these calculations from module 24*a* to another module. Because of the high speed communication abilities of Ethernet 26, such remote processing of feedback calculations can be accomplished without diminishing the control of the motors or actuators. Once the recipient module of the feedback data processes the received feedback data, it transmits the processed results back to motion control module 24*a* for use in controlling the one or more components of person support apparatus 20.

In any of the communication systems 22, 222, 422, and 622 described above, one or more additional modules 24 can be provided that perform any one or more of the following functions, whether alone or in combination with other functions. Alternatively, one or more of the previously described modules 24 can be modified to additionally perform one or more of the following functions: transmitting and/or displaying live video images, such as nurse call video transmitted to a display on a siderail of bed and/or Skype and/or Facetime video data; transmitting and/or playing audio, such as the audio of phone calls, audio that accompanies live video, audio from entertainment and/or audio translations of language; recognizing voices and voice commands from patients and/or caregiver via microphones that are located in close proximity to person support apparatus 20; and running higher level software applications over the Ethernet, which executes on lower layers of the OSI (Open Systems Interconnection) model.

FIGS. 7-9 illustrate several additional alternative embodiments of person support apparatus that are implemented as a stretcher 20*a*, a recliner 20*b*, and a cot 20*c*, respectively. Each of the person support apparatus 20*a*-20*c* includes an Ethernet 26 (not shown) that communicatively couples together a plurality of modules 24. FIG. 10 illustrates a thermal control unit 64 that is used to control the temperature of a fluid provided to one or more thermal pads that are positioned in close proximity to a patient, and thereby control the temperature of the patient. In one embodiment, thermal control unit 64 is constructed and operates in the manners disclosed in commonly assigned U.S. patent application Ser. No. 14/282,383 filed May 20, 2014 by inventors Christopher Hopper et al. and entitled THERMAL CONTROL SYSTEM, the complete disclosure of which is hereby incorporated herein by reference. Other constructions of thermal control units are also possible. Thermal control unit 64 includes a plurality of modules 24 that communicate with each other over an Ethernet 26 (not shown). Such modules include a Human Machine Interface (HMI) module 24*l*, a thermal system node 24*m*, a fluid system node 24*n*, and a control system node 24. HMI module 24*l* controls a touch screen and/or other user interface that enables a user to control control unit 64. Thermal system node 24*m* controls the heater/chiller in unit 64. Fluid system module 24*n* controls the pumping of fluid throughout the system, and control system node 24*o* controls the overall operation of unit 64.

FIG. 11 illustrates a plurality of discrete devices, such as multiple person support apparatuses 20 and 20*b*, as well as a thermal control unit 64, that are each in communication with each other. A cross-device Ethernet network is formed by the communication between modules 24 in each of these devices. Any of the data discussed above may be shared between these devices using this cross-device network.

It will be understood by those skilled in the art that, although many of the concepts and principles discussed herein have been described in conjunction with Ethernet 26, these concepts and principles can be implemented with other types of networks, such as, but not limited to, a Controller Area Network (CAN), a Local Interconnect Network (LIN), a Firewire network, and still others.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:
1. A person support apparatus comprising:
a frame;
a support surface supported on the frame and adapted to support a person, the support surface including a back section and a seat section;

a first module adapted to perform a first function associated with the person support apparatus;

a second module adapted to perform a second function associated with the person support apparatus;

a first communication network defining a first path from the first module to the second module, the first communication network adapted to transport data between the first and second modules over the first path using a first communication protocol, the first path residing entirely on the person support apparatus; and a second communication network defining a second path from the first module to the second module, the second communication network adapted to transport data between the first and second modules over the second path using a second communication protocol, the second communication protocol being different from the first communication protocol, and the second path residing entirely on the person support apparatus.

2. The person support apparatus of claim 1 wherein the first communication protocol is an Ethernet protocol, and the second communication protocol is one of the following: an RS-485 protocol, a serial peripheral interface (SPI) protocol, an RS-232 protocol, an RS-422 protocol, and an I-squared C protocol ($I^2C$).

3. The person support apparatus of claim 1 wherein the first communication network transports video data and the second communication network transports commands for moving at least one component of the person support apparatus.

4. The person support apparatus of claim 1 further comprising a third module adapted to perform a third function associated with the person support apparatus, the third module coupled to the first and second modules by the first communication network.

5. The person support apparatus of claim 4 wherein the first module includes a first microcontroller and an Ethernet switch, the second module includes a second microcontroller, the third module includes a third microcontroller.

6. The person support apparatus of claim 5 wherein the first microcontroller is adapted to control the Ethernet switch such that messages are routed over the first communication network between a subset of the first, second, and third modules.

7. The person support apparatus of claim 4 wherein the first function includes displaying graphics on a display of the person support apparatus, the second function includes controlling movement of the support surface, and the third function includes communicating with a device physically separate from the person support apparatus.

8. The person support apparatus of claim 7 further comprising a fourth module adapted to perform a fourth function associated with the person support apparatus, the fourth module coupled to the first, second, and third modules by the first communication network.

9. The person support apparatus of claim 8 wherein the fourth function includes driving a wheel coupled to the person support apparatus.

10. The person support apparatus of claim 1 wherein the first module includes a first microcontroller, the second module includes a second microcontroller, and the first microcontroller is adapted to decide whether to transmit a first message to the second module using the first communication network or the second communication network.

11. The person support apparatus of claim 10 wherein the first microcontroller decides whether to transmit the first message using the first communication network or the second communication network based upon a content of the first message.

12. The person support apparatus of claim 1 wherein the first module includes a first media access control (MAC) address and a first Internet Protocol (IP) address, the second module includes a second media access control (MAC) address and a second Internet Protocol (IP) address, and the first module is adapted to communicate with the second module over the first communication network by sending messages that include both the first and second MAC addresses and both the first and second IP addresses.

13. The person support apparatus of claim 2 wherein the person support apparatus is a bed, the first module is physically coupled to a frame of the bed, and the second module is physically positioned inside of a mattress positioned on top of the bed.

14. The person support apparatus of claim 2 wherein the person support apparatus is a bed having a support deck adapted to support a patient thereon, the first module is adapted to control movement of the support deck, and the second module is adapted to control movement of a drive wheel used to power movement of the bed from one location to another.

15. The person support apparatus of claim 1 wherein the first module is adapted to transmit a first command to the second module over both the first and second communication networks, and the second module is adapted to follow the first command if the second module receives the first command from the second communication network but does not receive the first command from the first communication network.

16. The person support apparatus of claim 15 wherein the second module is adapted to not follow the first command if the second module receives the first command from the first communication network but does not receive the first command from the second communication network, and wherein the second module is adapted to follow the first command if the second module receives the first command from both the first and second communication networks.

17. The person support apparatus of claim 15 wherein the first command instructs the second module to physically move a component of the person support apparatus.

18. The person support apparatus of claim 1 wherein the person support apparatus is a bed, the first module is physically coupled to a frame of the bed and includes a serializer/deserializer output for transmitting image data to a display mounted on a footboard of the bed, the image data being transmitted to the display in scalable vector graphics (SVG) format.

19. The person support apparatus of claim 18 wherein the first module receives a size message from the display indicative of a physical size of the display, and the first module adjusts the image data transmitted by the first module to the display based upon the size message, whereby different footboards may be coupled to the bed having different sized displays without requiring reprogramming of the first module.

* * * * *